US007632634B2

(12) United States Patent
Ahmed et al.

(10) Patent No.: US 7,632,634 B2
(45) Date of Patent: Dec. 15, 2009

(54) METHOD AND ASSAY FOR EARLY DIAGNOSIS OF PROSTATE CANCER

(75) Inventors: Hafiz Ahmed, Aldie, VA (US); Gerardo R. Vasta, Columbia, MD (US)

(73) Assignee: University of Maryland Biotechnology Institute, Baltimore, MD (US)

( * ) Notice: Subject to any disclaimer, the term of this patent is extended or adjusted under 35 U.S.C. 154(b) by 147 days.

(21) Appl. No.: 11/405,238

(22) Filed: Apr. 17, 2006

(65) Prior Publication Data

US 2006/0246496 A1    Nov. 2, 2006

Related U.S. Application Data

(60) Provisional application No. 60/672,171, filed on Apr. 15, 2005.

(51) Int. Cl.
*C12Q 1/68* (2006.01)

(52) U.S. Cl. .............................................. 435/4; 435/6

(58) Field of Classification Search ....................... None
See application file for complete search history.

(56) References Cited

U.S. PATENT DOCUMENTS 7,252,935 B2    8/2007    Sidransky

OTHER PUBLICATIONS

Chiariotti et al Biochimie vol. 81 p. 381 (1999).*
Ellerhorst et al Urol. Res. (1999) vol. 27 p. 362.*
Warnecke et al Current Opinion in Oncology vol. 12 p. 68 (2000).*
Herman et al, New England Journal of Medicine, vol. 349 p. 2042 (2003).*
Iurisci et al Clin. Cancer Res. vol. 6 p. 1389 (2000).*
Ahmed, Hafiz, et al., "Galectins: conservation of functionally and structurally relevant amino acid residues defines two types of . . . ", "Glycobiology", 1994, pp. 545-549, vol. 4, No. 5.
Ahmed, Hafiz, et al., "The primary structure and carbohydrate specificity of a beta-galactosyl-binding lectin from toad (bufo arenarum . . . ", "The Journal of Biological Chemistry", 1996, pp. 33083-33094, vol. 271, No. 51.
Ahmed, Hafiz, et al., "Novel carbohydrate specificity of the 16-kDa galectin from *Caenorhabditis elegans*: binding to blood group precursor . . . ", "Glycobiology", 2002, pp. 451-461, vol. 12, No. 8.
Ahmed, Hafiz, et al., "Biochemical and molecular characterization of galectins from zebrafish (Danio rerio): notochord-specific expression . . . ", "Glycobiology", 2004, pp. 219-232, vol. 14, No. 3.
Akahani, Shiro, et al., "Galectin-3: a novel antiapoptotic molecule with a functional BH1 (NWGR) domain of Bcl-2 family", "Cancer Research", Dec. 1, 1997, pp. 5272-5276, vol. 57.
Avni, Orly, et al., "Complement receptor 3 of macrophages is associated with galectin-1-like protein", "J. Immunol.", 1998, pp. 6151-6158, vol. 160.
Barondes, Samuel H., et al., "Galectins. Structure and function of a large family of animal lectins", "The Journal of Biological Chemistry", Aug. 19, 1994, pp. 20807-20810, vol. 269, No. 33.

Benvenuto, Giovanna, et al., "Cell-specific transcriptional regulation and reactivation of galectin-1 gene expression are controlled by DNA . . . ", "Molecular and Cellular Biology", Jun. 1996, pp. 2736-2743, vol. 16, No. 6.
Caplan, Aaron, et al., "Prostate-specific antigen and the early diagnosis of prostate cancer", "Am. J. Clin. Pathol.", 2002, pp. S104-S108, vol. 117 (Suppl 1).
Cho, Moonjae, et al., "Galectin-1, a beta-galactoside-binding lectin in Chinese hamster ovary cells", "The Journal of Biological Chemistry", Mar. 10, 1995, pp. 5207-5212, vol. 270, No. 10.
Colnot, Celine, et al., "The role of galectins in mouse development", "Trends in Glycoscience and Glycotechnology", Jan. 1997, pp. 31-40, vol. 9, No. 45.
Cooper, Douglas N. W., et al., "Evidence for export of a muscle lectin from cytosol to extracellular matrix and for a novel secretory mechanism", "The Journal of Cell Biology", May 1, 1990, pp. 1681-1691, vol. 110.
Cooper, Douglas N. W., et al., "Endogenous muscle lectin inhibits myoblast adhesion to laminin", "The Journal of Cell Biology", Dec. 1, 1991, pp. 1437-1448, vol. 115, No. 5.
Costa, M., et al., "Abstract Only: Galectin-3 gene expresssion is silenced by methylation of its promoter in murine melanoma cells", "Accessed Online at: http://web.archive.org/web/20050223095849/ http://direxlim.fm.usp.br/ r24b.php", 2003.
Fackler, Mary Jo, et al., "Quantitative multiplex methylation-specific PCR assay for the detection of promoter hypermethylation in multiple genes..", "Cancer Research", Jul. 1, 2004, pp. 4442-4452, vol. 64.
Frommer, Marianne, et al., "A genomic sequencing protocol that yields a positive display of 5-methylcytosine residues in individual DNA strands", "Proc. Natl. Acad. Sci. USA", Mar. 1992, pp. 1827-1831, vol. 89.
Gauthier, Laurent, et al., "Galectin-1 is a stromal cell ligand of the pre-B cell receptor (BCR) implicated in synapse formation between pre-B . . . ", "Proc. Natl. Acad. Sci. USA", Oct. 1, 2002, pp. 13014-13019, vol. 99, No. 20.
Gibson, Ursula E.M., et al., "A novel method for real time quantitative RT-PCR", "Genome Research", 1996, pp. 995-1001, vol. 6.
Glinsky, Vladislav V., et al., "Effects of Thomsen-Friedenreich antigen-specific peptide P-30 on beta-galactoside-mediated homotypic aggregation and . . . ", "Cancer Research", May 15, 2000, pp. 2584-2588, vol. 60.
Glinsky, Vladislav V., et al., "The role of Thomsen-Friedenreich antigen in adhesion of human breast and prostate cancer cells to the endothelium", "Cancer Research", Jun. 15, 2001, pp. 4851-4857, vol. 61.
Goletz, Steffen, et al., "Novel alphaGalNAc containing glycans on cytokeratins are recognized in vitro by galectins with type II carbohydrate . . . ", "Journal of Cell Science", 1997, pp. 1585-1596, vol. 110.
Gong, Hua Chang, et al., "The NH2 terminus of galectin-3 governs cellular compartmentalization and functions in cancer cells", "Cancer Research", Dec. 15, 1999, pp. 6239-6245, vol. 59.

(Continued)

*Primary Examiner*—Sheela J Huff
(74) *Attorney, Agent, or Firm*—Kelly K. Reynolds; Steven J. Hultquist; Intellectual Property/Technology Law

(57) ABSTRACT

A method and assay are described for determining prostate cancer and the general stage of progression of such cancer by quantifying levels of expression of different galectin isoforms and/or different levels of promoter methylation of such galectin isoforms.

8 Claims, 10 Drawing Sheets

OTHER PUBLICATIONS

Gu, Maojian, et al., "Selective modulation of the interaction of alpha7beta1 integrin with fibronectin and laminin by L-14 lectin during . . . ", "Journal of Cell Science", 1994, pp. 175-181, vol. 107.
Hadari, Yaron R., et al., "Galectin-8 binding to integrins inhibits cell adhesion and induces apoptosis", "Journal of Cell Science", 2000, pp. 2385-2397, vol. 113.
Hanahan, Douglas, et al., "The hallmarks of cancer", "Cell", Jan. 7, 2000, pp. 57-70, vol. 100.
Heid, Christian A., et al., "Real time quantitative PCR", "Genome Research", 1996, pp. 986-994, vol. 6.
Herman, James G., et al., "Methylation-specific PCR: a novel PCR assay for methylation status of CpG islands", "Proc. Natl. Acad. Sci.", Sep. 1, 1996, pp. 9821-9826, vol. 93, Published in: Washington, D.C., US.
Hernandez, Joseph D., et al., "Ah, sweet mystery of death! Galectins and control of cell fate", "Glycobiology", 2002, pp. 127R-136R, vol. 12, No. 10.
Inohara, Hidenori, et al., "Functional evidence that cell surface galectin-3 mediates homotypic cell adhesion", "Cancer Research", Aug. 1, 1995, pp. 3267-3271, vol. 55.
Iurisci, Ida, et al., "Concentrations of galectin-3 in the sera of normal controls and cancer patients", "Clinical Cancer Research", Apr. 2000, pp. 1389-1393, vol. 6.
Leffler, Hakon, et al., "Specificity of binding of three soluble rat lung lectins to substituted and unsubstituted mammalian beta-galactosides", "The Journal of Biological Chemistry", Aug. 5, 1986, pp. 10119-10126, vol. 261, No. 22.
Levy, Yifat, et al., "Galectin-8 functions as a matricellular modulator of cell adhesion", "The Journal of Biological Chemistry", Aug. 17, 2001, pp. 31285-31295, vol. 276, No. 33.
Liao, Der-Ing, et al., "Structure of S-lectin, a developmentally regulated vertebrate beta-galactoside-binding protein", "Proc. Natl. Acad. Sci. USA", Feb. 1994, pp. 1428-1432, vol. 91.
Nangia-Makker, Pratima, et al., "Galectin-3 induces endothelial cell morphogenesis and angiogenesis", "American Journal of Pathology", Mar. 2000, pp. 899-909, vol. 156, No. 3.
Park, Jung W., et al., "Association of galectin-1 and galectin-3 with gemin4 in complexes containing the SMN protein", "Nucleic Acids Research", 2001, pp. 3595-3602, vol. 27, No. 17.
Rosenberg, Ian, et al., "Mac-2-binding glycoproteins", "The Journal of Biological Chemistry", Oct. 5, 1991, pp. 18731-18736, vol. 266, No. 28.
Rubinstein, Natalia, et al., "Targeted inhibition of galectin-1 gene expression in tumor cells results in heightened T cell-mediated rejection: . . . ", "Cancer Cell", Mar. 2004, pp. 241-251, vol. 5.
Singal, Rakesh, et al., "Cytosine methylation represses glutathione S-transferase P1 (GSTP1) gene expression in human prostate cancer cells", "Cancer Research", Jun. 15, 2001, pp. 4820-4826, vol. 61.
Stewart, Delisha A., et al., "Changes in extracellular matrix (ECM) and ECM-associated proteins in the metastatic progression of prostate cancer", "Reprod. Biol. Endocrinol.", 2004, pp. 2-14, vol. 2.
Su, Zao-Zhong, et al., "Surface-epitope masking and expression cloning identifies the human prostate carcinoma tumor antigen gene PCTA-1 . . . ", "Proc. Natl. Acad. Sci. USA", Jul. 1996, pp. 7252-7257, vol. 93.
Symons, Antony, et al., "Characterization of the interaction between galectin-1 and lymphocyte glycoproteins CD45 and Thy-1", "Glycobiology", 2000, pp. 559-563, vol. 10, No. 6.
Thompson, Ian M., et al., "Prevalence of prostate cancer among men with a prostate-specific antigen level less than or equal to 4.0 ng per ML", "New Eng. J. Med.", May 27, 2004, pp. 2239-2246, vol. 350, No. 22.
Vasta, Gerardo R., et al., "Galectins from amphibian species: carbohydrate specificity, molecular structure and evolution", "Trends in Glycoscience and Glycotechnology", Jan. 1997, pp. 131-144, vol. 9, No. 45.
Yang, Ri-Yao, et al., "Expression of galectin-3 modulates T-cell growth and apoptosis", "Proc. Natl. Acad. Sci. USA", Jun. 1996, pp. 6737-6742, vol. 93.

Yang, Ri-Yao, et al., "Cell cycle regulation by galectin-12, a new member of the galectin superfamily", "The Journal of Biological Chemistry", Jun. 8, 2001, pp. 20252-20260, vol. 276, No. 23.
Yu, Fei, et al., "Galectin-3 translocates to the perinuclear membranes and inhibits cytochrome c release from the mitochondria", "The Journal of Biological Chemistry", May 3, 2002, pp. 15819-15827, vol. 277, No. 18.
Ahmed, Hafiz, et al., "Human Splenic galaptin: carbohydrate binding specificity and characterization of the combining site", "Biochemistry", 1990, pp. 5315-5319, vol. 29, No. 22.
Ahmed, Hafiz, et al., "Lymphoblastoid cell adhesion mediated by a dimeric and polymeric endogenous beta-galactoside-binding lectin (Galaptin)", "Journal of Molecular Recognition", 1992, pp. 1-8, vol. 5.
Ahmed, Hafiz, et al., "A novel solid phase assay for Lectin binding", "Ann. N.Y. Acad. Sci.", 1994, pp. 315-317, vol. 712.
Ahmed, Hafiz, et al., "Elasmobranch and Teleost Fish Contain Thiol-Dependent Beta-Galactoside-Binding Lectins That Are Cross-Reactive With . . . ", "Ann. N.Y. Acad. Sci.", 1994, pp. 318-320, vol. 712.
Ahmed, H. et al., "Galectin-1 from Bovine Spleen: Biochemical Characterization, Carbohydrate Specificity and Tissue-Specific Isoform . . . ", Oct. 5, 1996, pp. 1007-1019, vol. 120.
Allen, H. et al., "Galaptin and Galaptin-Binding Glycoconjugates in Serum and Effusions of Carcinoma Patients", "Tumor Biology", 1993, pp. 360-368, vol. 14.
Bianchet, M. et al., "Soluble Beta-Galactosyl-Binding Lectin (Galectin) From Toad Ovary: Crystallographic Studies of Two Protein-Sugar Complex", "Proteins: Structure, Function, and Genetics", 2000, pp. 378-388, vol. 40.
Bidon, N. et al. , "Two messenger RNAs and five isoforms for Po66-CBP, a galectin-8 homolog in a human lung carcinoma cell line", "Gene", 2001, pp. 253-262, vol. 274.
Bidon-Wagner, N. et al., "Human Galectin-8 isoforms and cancer", "Gycoconjugate Journal", 2004, pp. 557-563, vol. 19.
Califice, S. et al., "Dual activities galectin-3 in human prostate cancer: tumor suppression of nuclear galectin-3 versus tumor promotion . . . ", "Oncogene", Aug. 23, 2004, pp. 7527-7536, vol. 23, Publisher: Nature Publishing Group.
Camby, I. et al., "Galectins Are Differentially Expressed in Supratentorial Pilocytic Astrocytomas, Astrocytomas, Anaplastic Astrocytomas..", "Brain Pathology", 2001, pp. 12-26, vol. 11.
Chiariotti, Lorenzo, et al., "Control of galectin gene expression", "Biochimie", 1999, pp. 381-388, vol. 81.
Colnot, Celine, et al., "Uncoupling of Chondrocyte Death and Vascular Invasion in Mouse Galectin 3 Null Mutant Bones", "Developmental Biology", Jan. 2001, pp. 203-214, vol. 229.
Cooper, D. , "Galectinomics: finding themes in complexity", "Biochimica et Biophysica Acta", 2002, pp. 209-231, vol. 1572.
Danguy, A. , "Immunohistochemical profile of galectin-8 expression in benign and malignant tumors of epithelial, mesenchymatous and . . . ", "Histology and Histopathology", 2001, pp. 861-868, vol. 16.
Ellerhorst, Julie, et al., "Galectin-1 and galectin-3 expression in human prostate tissue and prostate cancer", "Urol. Res.", 1999, pp. 362-367, vol. 27.
Ellerhorst, Julie, et al., "Differential expression of endogenous galectin-1 and galectin-3 in human prostate cancer cell lines and effects of . . . ", "Int J Oncol.", 1999, pp. 217-224, vol. 14.
Gotz, W. et al., "Detection and distribution of the carbohydrate binding protein galectin-3 in the human notochord, invertebral disc . . . ", "Differentiation", 1997, pp. 149-157, vol. 62.
Hirabayashi, J. et al., "The family of metazoan metal-independent beta-galactoside binding lectins: structure, function, and molecular evolution", "Glycobiology", 1993, pp. 297-304, vol. 3, No. 4.
Jain, S. et al. , "Improving the utility of prostate specific antigen (PSA) in the diagnosis of prostate cancer: the use of PSA derivatives", "Postgrad. Med. J.", 2002, pp. 646-650, vol. 78.
Jones, P. et al. , "The Fundamental Role of Epigenetic Events in Cancer", "Nature Reviews Genetics", Jun. 2002, pp. 415-428, vol. 3.
Kadrofske, M. et al., "The Human LGALS3 (Galectin-3) Gene: Determination of the Gene Structure and Functional Characterization of the Promoter", "Archives of Biochemistry and Biophysics", Jan. 1, 1998, pp. 7-20, vol. 349, No. 1.

Keetch, D. et al., "Serial Protastic Biposies in Men With Persistently Elevated Serum Prostate SPpecific Antigen Values", "The Journal of Urology", Jun. 1994, pp. 1571-1574, vol. 151.

Kondoh, N. et al., "Activation of Galectin-1 gene in human hepatocellular carcinoma involves methylation-sensitive complex formations at . . . ", "Int J Oncol.", 2003, pp. 1575-1583, vol. 23.

Leffler, Hakon, et al., "Introduction to galectins", "Glycoconjugate Journal", 2004, pp. 433-440, vol. 19.

Liu, F., "Short Analytical Review: Galectins: A New Family of Regulators of Inflammation", "Clinical Immunology", Nov. 2000, pp. 79-88, vol. 97, No. 2.

Liu, F. et al., "Galectins as Modulators of Tumour Progression", "Nature Reviews: Cancer", Jan. 2005, pp. 29-41, vol. 5.

Matarrese, P. et al., "Galectin-3 Overexpression Protects From Apoptosis by Improving Cell Adhesion Properties", "Int. J. Cancer", 2000, pp. 545-554, vol. 85.

Mizejewski, G., "Role of Integrins in Cancer: Survey of Expression Patterns", "Intergrins Expression in Cancer", 1999, pp. 124-138, Publisher: Society for the Experimental Biology and Medicine.

Nagia-Makker, P. et al., "Carbohydrate-binding proteins in cancer, and their ligands as therapeutic agents.", "Trends in Molecular Medicine", Apr. 2002, p. 2002 vol. 8, No. 4.

Ozeki, Y. et al., "Tissue fibronection is an endogenous ligand for galectin-1", "Glycobiology", 1995, pp. 255-261, vol. 5, No. 2.

Pacis, R. et al., "Decreased Galectin-3 Expression in", "The Prostate", 2000, pp. 118-123, vol. 44.

Paz, A. et al., "Galectin-1 binds oncogene H-Ras to mediate Ras membrane anchorage and cell transfomration", "Oncogene", Sep. 2001, pp. 7486-7493, vol. 20, Publisher: Nature Publishing Company.

Perillo, N. et al., "Apotosis of T-Cells Mediated by Galectin 1", "Letters to Nature", Dec. 14, 1995, pp. 736-739, vol. 378, Publisher: Nature.

Perillo, N. et al., "Galectins: Versatile modulators of cell adhesion, cell proliferation, and cell death", "J Mol. Med", 1998, pp. 402-412, vol. 76.

Puche, A. et al., "Role of Galectin-1 in the Developing Mouse olfactory system", "Developmental Biology", 1996, pp. 274-287, vol. 179, Publisher: Academic Press Inc.

Rabinovich, G. et al., "Role of galectins in inflammatory and immunomodulatory processes", "Biochimica et Biophysica Acta", 2002, pp. 274-284, vol. 1572.

Rabinovich, G. et al., "Shedding Light on the Immunomodulatory properties of galectins", "Glycoconjugate Journal", 2004, pp. 565-573, vol. 19.

Salvatore, P. et al., "High resolution methylation analysis of the galectin-1 gene promoter region in expressing and nonexpressing tissues", "FEBS Letters", 1998, pp. 152-158, vol. 421.

Schwarz, F. et al., "Thermodynamics of Bovine Spleen Galectin-1 Binding to Disaccharides: Correlation with Structure and Its Effect on . . . ", "Biochemistry", 1998, pp. 5867-5877, vol. 37, No. 17.

Van Den Brule, S. et al., "Increased expression of galectin-1 in carcinoma associated stroma predicts poor outcome in prostate carcinoma patients", "J. Pathol.", 2001, pp. 80-87, vol. 193.

Van Den Brule, S. et al., "Expression of Galectins in Cancer: a critical review", "Glycoconjugate Journal", 2004, pp. 537-542, vol. 19.

Vasta, G. et al., "C-type lectins and galectins mediate innate and adaptive immune functions: their roles in the complement activation . . . ", "Developmental and Comparative Immunology", 1999, pp. 401-420, vol. 23.

Vasta, Gerardo R., et al., "Galectins in telost fish: Zebrafish (Danio rerio) as a model species to address their biological riles in development . . . ", "Glycoconjugate Journal", Jan. 2004, pp. 503-521, vol. 21.

Vasta, G. et al., "Structural and functional diversity of lectin repertoires in invertebrates, protochordates and ectothermic vertebrates", "Current Opinion in Structural Biology", 2004, pp. 617-630, vol. 14.

Warfiled, P. et al., "Adhesion of Human Breast Carcinoma to Extracellular Matrix Proteins is Modulated by Galectin-3", "Invasion Metastasis", 1997, pp. 101-112, vol. 17.

Warnecke, Peter M., et al., "Cytosine methylation and human cancer", "Current Opinion in Oncology", 2000, pp. 68-73, vol. 12.

Zhou, Q. et al., "L-14 Lectin Recognition of Laminin and Its Promotion of in Vitro Cell Adhesion", "Archives of Biochemistry and Biophysics", Jan. 1993, pp. 6-17, vol. 300, No. 1.

Zick, Y. et al., "Role of galectin-8 as a modulator of cell adhesion and cell growth", "Glycoconjugate Journal", 2004, pp. 517-526, vol. 19.

* cited by examiner

METHOD AND ASSAY FOR EARLY DIAGNOSIS OF PROSTATE CANCER

CROSS-REFERENCE TO RELATED APPLICATION

The benefit of priority of U.S. provisional patent application 60/672,171 filed Apr. 15, 2005 in the names of Hafiz Ahmed and Gerardo R. Vasta for "A Novel Approach for Early Diagnosis of Prostate Cancer," is hereby claimed under the provisions of 35 USC 119.

GOVERNMENT SUPPORT

This invention was made with Government support under Grant No. 1R01 GM070589-01 awarded by the National Institutes of Health's National Institute of General Medical Sciences. The Government has certain rights in this invention.

BACKGROUND OF THE INVENTION

1. Field of the Invention

The present invention relates to detection of prostate cancer, and more particularly, to a non-invasive method for the accurate diagnosis of prostate cancer by determining and comparing galectin expression and/or promoter methylation of galectins.

2. Related Art

Prostate cancer is the second most common cancer in men (after skin cancer), and the second leading cause of cancer death in men (after lung cancer). In the United States, there are greater than 300,000 newly diagnosed cases each year, and about 40,000 of patients die of the disease yearly (Stewart et al., 2004). Approximately 90% of patients with advanced prostate cancer develop osseous metastases. Once prostate cancer metastasizes to the bone it is difficult to eradicate, and typically, these patients have a mean survival time of nine months to one year (Stewart et al., 2004).

Approximately 30% of men over the age of 55 harbor latent prostate cancers, detectable only at postmortem examination. Greater than 95% of cancers of the prostate are gland-forming adenocarcinomas, which have a predilection for the peripheral zones. The remaining prostate cancers are divided between squamous cell and transitional cell carcinomas (arising from the prostatic ducts), small cell and other neuroendocrine tumors, and rarely, carcinosarcomas. The histologic precursor lesion of prostatic adenocarcinomas is prostatic intraepithelial neoplasia (PIN), which shares the cytological features of cancer as well as many of the associated genetic abnormalities. Unlike adenocarcinomas, PIN occurs within preexisting acinar structures, and is divided into low-grade (meaning slightly unusual) and high-grade (very unusual and close to being called cancer) variants. The latter is a more reproducible diagnosis and also has a stronger morphologic, genetic and clinical association with prostate cancer. In fact, the presence of isolated high-grade PIN in needle biopsy specimens strongly suggests that there is a co-existing carcinoma in the prostate.

Although a considerable proportion of prostate cancers grow slowly and are not considered to require urgent intervention, some grow quickly and are deadly. When these are detected in early stages, however, they can be effectively treated and cured. Combined with the digital rectal examination (DRE), the prostate specific antigen (PSA) test has been widely used to detect prostate cancer in its early stages. This test measures the serum levels of PSA, an enzyme that is produced by the prostate and released into the bloodstream to reach concentrations below 3-4 ng/ml in healthy individuals. PSA levels above that value are considered as an indication of possible prostate cancer. However, PSA is specific for prostate tissues, but not for prostate cancer. Multiple factors such as benign prostatic hyperplasia (BPH), prostatitis, prostatic ischemia or infarction, and even sexual activity can cause of elevated levels of PSA. Further, serum PSA levels are not a sensitive indicator for prostate cancer, as these may be normal despite the presence of the disease (Thompson et al., 2004).

Thus, the PSA screening method for early detection of prostate cancer is flawed by potential false positive and false negative results. False positives may lead to additional medical procedures that have potential risks, represent significant financial costs, and create anxiety for the patient and his family. Actually, only 25 to 30 percent of men who have a biopsy due to elevated PSA levels are diagnosed with prostate cancer (Keetch et al., 1994). Several modifications of the standard PSA test have been developed, and may be beneficial for select populations (Caplan and Kratz, 2002). However, uncertainty about the natural progression of prostate cancer and inherent limitations of PSA test raises serious concerns about the reliability and potential benefits of universal screening, and the recommendations of various organizations are conflictive (Caplan and Kratz, 2002).

Attempts to relate cancer-related PSA to PSA density using transrectal ultrasound or to relate PSA to velocity of change with time have been helpful but flawed (Jain et al., 2002). PSA forms complexes with various serum factors, including alpha 1-antichymotrypsin, and such complex formation is significantly higher in PC than in benign prostatic conditions; in general, the higher the proportion of free PSA, the lower the risk of cancer (Jain et al., 2002). Since there is a tendency to biopsy all individuals with PSA values above 3.5-4.0, using the "free" PSA to total PSA ratio could reduce negative prostate biopsies by 21-35%. Therefore, the test may be helpful in deciding whether a biopsy should be done. However, PSA cannot be used as a prognostic marker.

A variety of prognostic markers have come recently into vogue as prognostic indicators in prostate cancers. For example, DNA aneuploidy in prostate cancers correlates with a higher stage disease and shortened survival. The role of MIB-1 labeling index as a measure of proliferation, bcl-2 expression, loss of E-cadherin expression, and abnormal p53 accumulation have been proposed as prognostic indicators. However, the search to identify "ideal" marker(s) that would foretell disease progression and aggressiveness in newly diagnosed prostate cancers is ongoing.

Therefore, markers that would rigorously diagnose the presence of the disease and serve as an indicator of disease progression and aggressiveness in prostate cancer is yet to be identified.

SUMMARY OF THE INVENTION

The present invention relates to methods for determining prostate cancer and the general stage of progression of such cancer by quantifying levels of expression of different galectin isoforms and/or different levels of promoter methylation of such galectin isoforms.

In one aspect, the present invention provides for a method to determine prostate cancer in a subject, the method comprising:
  obtaining a biological sample from the subject;
  determining levels of expression of at least one galectin isoform; and
  comparing the levels of expression relative to levels found in normal prostate tissue.

In another aspect, the present invention provides for a method to determine prostate cancer in a subject, the method comprising:
    obtaining a biological sample from the subject;
    determining the levels of expression of Gal3 and Gal8g; and
    comparing the levels of expression relative to levels found in normal prostate tissue, wherein an increase of Gal8g expression and a decrease of Gal3 expression is an indication of prostate cancer.

In yet another aspect, the present invention relates to a method for determining prostate cancer in a subject, the method comprising:
    obtaining a biological sample from the subject;
    determining the levels of methylation of at least one galectin isoform; and
    comparing the level of methylation relative to a level found in the isoform from normal prostate tissue.

In still another aspect, the present invention relates to a method for determining prostate cancer in a subject, the method comprising:
    obtaining a biological sample from the subject;
    determining the levels of promoter methylation of Gal3 and Gal8g; and
    comparing the levels of promoter methylation relative to levels found in normal prostate tissue, wherein a decrease of Gal8g promoter methylation and an increase of Gal3 promoter methylation is an indication of prostate cancer.

In another aspect, the present invention relates to an assay for determining prostate cancer in a subject, the method comprising:
    providing a coating of a known amount of an anti-galectin isoform antibody;
    contacting the coating with a biological sample of the subject, wherein isoform will bind to the anti-antibody;
    adding an additional amount of soluble anti-galectin isoform antibody for additional binding to the previously bound isoform;
    adding a secondary tagged antibody for binding with the soluble anti-galectin isoform antibody to introduce a reporter marker; and
    determining the level of binding of galectin isoform to a standard curve, wherein an increase in the reporter marker indicates prostate cancer.

In yet another aspect, the present invention relates to an assay for determining prostate cancer in a subject, the method comprising:
    providing a coating of a known amount of an anti-galectin antibody selected from anti-gal3 or anti-gal8g;
    contacting the coating with a biological sample of the subject, wherein gal3 or gal8g will bind to the anti-antibody;
    adding additional amount of the anti-gal3 or anti-gal8g antibody for binding to gal3 or gal8g;
    adding a secondary antibody for binding with the anti-gal3 or anti-gal8g antibody to introduce a reporter marker; and
    determining the level of binding of gal3 or gal8 relative to a standard curve, wherein an increase in the reporter marker indicates prostate cancer.

In yet another aspect, the present invention relates to an assay for determining prostate cancer in a subject, the method comprising:
    a) providing a coating of a known amount of gal3 or gal8g;
    b) mixing a known amount of anti-galectin antibody selected from anti-gal3 or anti-gal8g with a biological sample from the subject, wherein the anti-galectin antibody will bind with any gal3 or gal8g in the sample;
    c) contacting the coating with the mixture of step (b);
    d) adding a secondary tagged antibody for binding with the anti-gal3 or anti-gal8g antibody to introduce a reporter marker; and
    e) measuring the binding of any soluble gal3 or gal8g in the biological sample to the anti-antibody to determine prostate cancer.

Another aspect of the present invention relates to an assay for determining prostate cancer in a subject, the method comprising:
    isolating a single-stranded DNA encoding Gal3 or Gal8g;
    treating the single-stranded DNA with bisulfite to convert non-methylated cytosine into uracil; and
    determining the level of methylation of the single stranded DNA, wherein a decrease of Gal8g promoter methylation and an increase of Gal3 promoter methylation is an indication of prostate cancer.

DETAILED DESCRIPTION OF THE INVENTION

Figure 1:
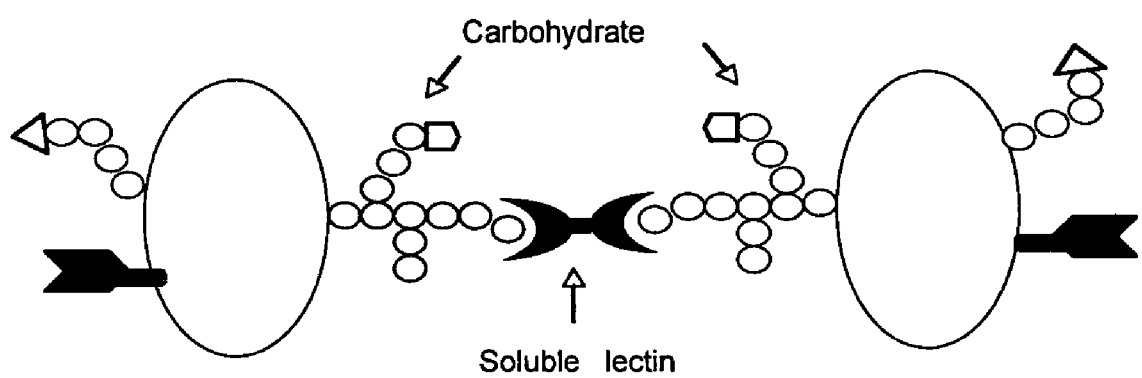
FIG. 1 is a schematic representation of lectin-carbohydrate-mediated cell-cell interaction. Lectins can be soluble or membrane-bound.

There is growing evidence that complex carbohydrate structures encode information that modulates interactions between cells, or cell and the extracellular matrix (ECM), by specifically binding to carbohydrate-binding proteins, such as galectins (Liu and Rabinovich, 2005; Rabinovich et al., 2004; Rubinstein et al., 2004) as shown in FIG. 1.

Figure 2:
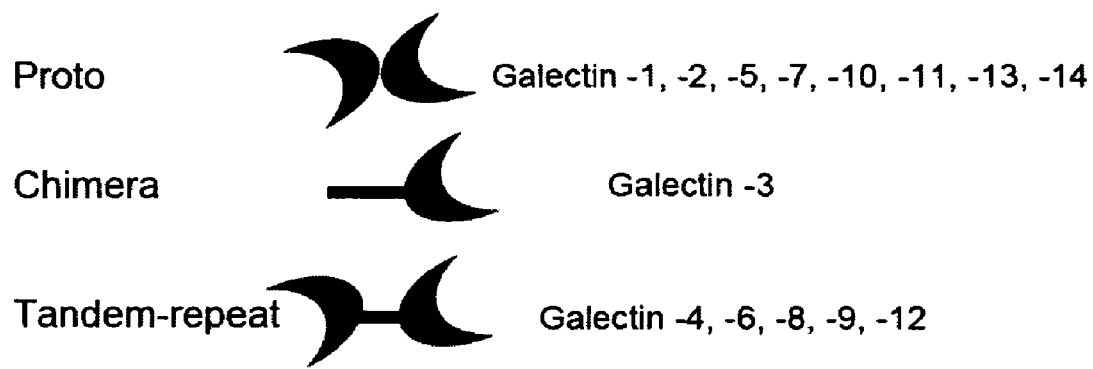
FIG. 2 shows the classification of galectins: Schematic representation of proton, chimera, and tandem-repeat type galectins. Multiple galectin members are known for proto- and tandem-repeat type. They are numbered according to the order of their discovery (Barondes et al., 1994; Leffler et al., 2004).

Galectins, an evolutionarily conserved family of β-galactoside-binding proteins (previously known as S-type lectins), have been identified in most animal taxa and fungi (Cooper, 2002; Leffer et al., 2004). They are present not only in the cytosol but also in the ECM (Cooper and Barondes, 1990; Cho and Cummings, 1995). Based on structural features, galectins have been classified in three types: "proto," "chimera," and "tandem-repeat" as shown in FIG. 2 (Hirabayashi and Kasai, 1993). Proto type galectins contain one "carbohydrate recognition domain" (CRD) per subunit, and usually form homodimers of non-covalently-linked subunits. The chimera type galectins have a C-terminal domain similar to the proto type, but exhibit an N-terminal domain that is responsible for interactions between subunits, and other CRD-independent functions. Tandem-repeat galectins, in which two CRDs are joined by a linker peptide, are monomeric. The dimerization of proto type galectins is critical for their function in mediating cell-cell or cell-ECM interactions (Barondes et al., 1994), and similar interactions via the N-terminus domain have been proposed for the chimera type galectins (Liu, 2000).

The galectins' ability to discriminate among carbohydrate structures is striking. Although galectins are β-galactoside-binding lectins, the relative binding affinity of either D-galactose or its α/β methyl derivative is almost 200 times less effective than that the β-galactose-containing disaccharide lactose (Lac) (Ahmed et al., 1990; 1996 a, b; 2004). For most galectins, N-acetyllactosamine (LacNAc) and thiodigalactoside (TDG) are 5-10 times more active than Lac. Close examination of carbohydrate-binding specificities of galectins, however, revealed diversity in their binding properties (Ahmed and Vasta, 1994). For example, the T-disaccharide is a good ligand for chimera galectins. The basis for the variable binding profiles of these galectins has been explained by their 3-D structures (Liao et al., 1994; Bianchet et al., 2000).

In the extracellular space, galectins bind to β-galactoside containing glycoproteins of ECM components and the cell surface adhesion molecules. These include laminin (Cooper et al., 1991; Zhou and Cummings, 1993), fibronectin (Ozeki et al., 1995), Thy-1 antigen (Symons et al., 2000), CD45 (Symons et al., 2000), α7β1 integrin (Gu et al, 1994), α3β1 integrin (Hadari et al., 2000), complement receptor CR3 (Avni et al., 1998), and Mac-2 binding protein (Rosenberg et al., 1991). However, the endogenous ligand of a particular galectin may vary from site to site (Leffler et al., 2004). In the intracellular space, galectins bind to their ligands, such as gemin 4 (Park et al., 2001), H-Ras (Paz et al., 2001), Bcl-2 (Yang et al., 1996), cytokeratin (Goletz et al., 1997), synexin (Yu et al., 2002) not only via protein-carbohydrate interactions, but also by protein-protein interactions. In the intracellular space, galectins are involved in mRNA splicing, cell cycle, cell proliferation, and apoptosis.

Galectins have been proposed to mediate diverse biological processes such as embryogenesis (Colnot et al., 1997; Ahmed et al., 2004), neuron projection (Puche et al., 1996), B cell development (Gauthier et al., 2002), inflammation (Liu, 2000, Rabinovich et al., 2002), apoptosis (Perillo et al., 1995, Hernandez and Baum, 2002), and tumor metastasis (Rubinstein et al., 2004; van den Brule et al., 2004; Liu and Rabinovich, 2005). The dynamic pattern of expression of gal1 and gal3 during mouse embryogenesis suggests that they have roles in notochord development, somitogenesis, development of central nervous system, and development of bone (Colnot et al., 1997, 2001; Gotz et al., 1997). The gal1 null mice are deficient in the development of a subset of olfactory neurons (Colnot et al., 1997).

Many epithelial tumors, such as colon, thyroid and breast carcinomas, express both gal1 and gal3. The increased expression of gal1 by tumor cells is positively correlated with a metastatic phenotype and a poorly differentiated morphology. Numerous reports indicate a direct correlation of gal3 expression with colon, head and neck, gastric, endometrial, thyroid and breast carcinomas, but some reports on colon and breast cancer present conflicting results (Nangia-Makker et al., 2002). Gal2, 4, and 9 were confined to a significant fraction of colorectal tumor cell lines. Gal1, 3 and 8 were involved in tumoral astrocyte invasion of the brain parenchyma (Camby et al., 2001). Ectopic expression of gal12 in cancer cells causes cell cycle arrest during G1 phase and cell growth suppression (Yang et al., 2001).

Galectins are also involved in cellular functions like cell-cell aggregation, cell-matrix adhesion, and invasion processes that could be important during cancer progression and metastasis. Breast cancer cells expressing gal3 demonstrated adhesion to laminin and collagen IV, but not fibronectin (Warfield et al., 1997). In blood vessels, tumor cells form emboli (cell aggregates), which protects them in the hostile host environment. It was demonstrated that when induced by asialofetuin, cell surface gal3 mediates homotypic aggregation (tumor embolus) (Inohara and Raz, 1995). Gal3 modulates integrin-ECM interactions. Integrins participate in intracellular signal transduction, which regulates cell proliferation, survival, differentiation, and motility (Mizejewski, 1999). Gal3 is also present on the endothelial cell surface and contributes to metastasis (Glinsky et al., 2001). Metastasis of cancer requires extravasation of cells, which involves binding of cells to endothelium. It has been demonstrated that Thomsen-Friedenreich antigen (T antigen), which has β-galactose as the terminal residue, interacts with the endothelial gal3 (Glinsky et al., 2000). Gal3 is involved in tumor related angiogenesis (Nangia Makker et al., 2000); it stimulates in vitro capillary tube formation by human umbilical endothelial cells (HUVEC) and in vivo neovascularization.

Gal8 positively or negatively regulates cell adhesion, depending on the extracellular context (Levy et al., 2001). When immobilized onto ECM, gal8 promotes cell adhesion, spreading, and migration through selective interactions with α3β1 and α6β1 integrins. Cell adhesion to gal8 triggers integrin-mediated signaling cascades such as Tyr phosphorylation of focal adhesion kinase (FAK) and paxillin. In contrast, excess soluble gal8 interacts both with cell surface integrins and with other soluble ECM proteins and inhibits cell-matrix interactions (Zick et al., 2004).

Resistance to apoptosis enables tumor cells to avoid programmed cell death induced by detachment from the ECM, and to survive the host immune defenses during passage through the circulatory system. Several studies suggest an anti-apoptotic effect of gal3 in a variety of human tumor cells. Induction of gal3 expression in a human leukemia T cell line (Yang et al., 1996) and breast cancer cells (Akahani et al., 1997) was found to confer resistance to cell death. Gal3 is the only member of the galectin family that contains the NWGR anti-death domain of the Bcl-2 family. Like Bcl-2, gal3 could be a mitochondria-associated apoptotic inhibitor (Matarrese et al., 2000), and a critical determinant for anchorage-independent and free radical-resistant cell survival during metastasis. Conversely, gal1 induces apoptosis of activated T cells and of both negatively selected and nonselected thymocytes (Perillo et al., 1998). Expression of gal1 protects tumor cells from immune surveillance by inducing the apoptosis of tumor infiltrating T cells (Rubinstein et al., 2004). Several human T cell leukemia lines are susceptible to gal1-induced apoptosis. Thus, although gal1 expression by carcinomas may favor tumor cell metastasis and a malignant phenotype, this protein may have therapeutic value for the treatment of hematopoietic malignancies because of its potential to induce apoptosis of leukemia cells (Perillo et al., 1998).

Initial screening of human primary prostate carcinoma revealed that gal1 was undetectable in normal, intraepithelial neoplasia or carcinoma cells, but present in the stroma, and associated fibroblasts (Van den Brule et al., 2001). Similarly, little or no expression of gal3 was observed in most prostate cancer cells. In those cases in which gal3 were detected, however, it was only in the cytoplasmic compartment (van den Brule et al., 2001). The role of gal3 in cancer progression was further examined by specifically expressing gal3 in either cytoplasm or nucleus of LNCaP, a gal3-negative human prostate cancer cell line (Califice et al., 2004). No changes in cell morphology, proliferation, attachment to laminin-1, or androgen dependency were observed. However, cytoplasmic gal3 significantly increased Matrigel invasion, anchorage-independent growth, in vivo tumor growth and angiogenesis, and decreased inducible apoptosis. Surprisingly, nuclear gal3 affected these parameters in an opposite fashion with an overall antitumoral activity (Califice et al., 2004). Several prostate cancer cell lines, including but not limited to PC-3, PC-3M, DU145, PrEC-1, and MCF10A express gal3, whereas LNCaP and TSU-prl do not.

Figure 3:
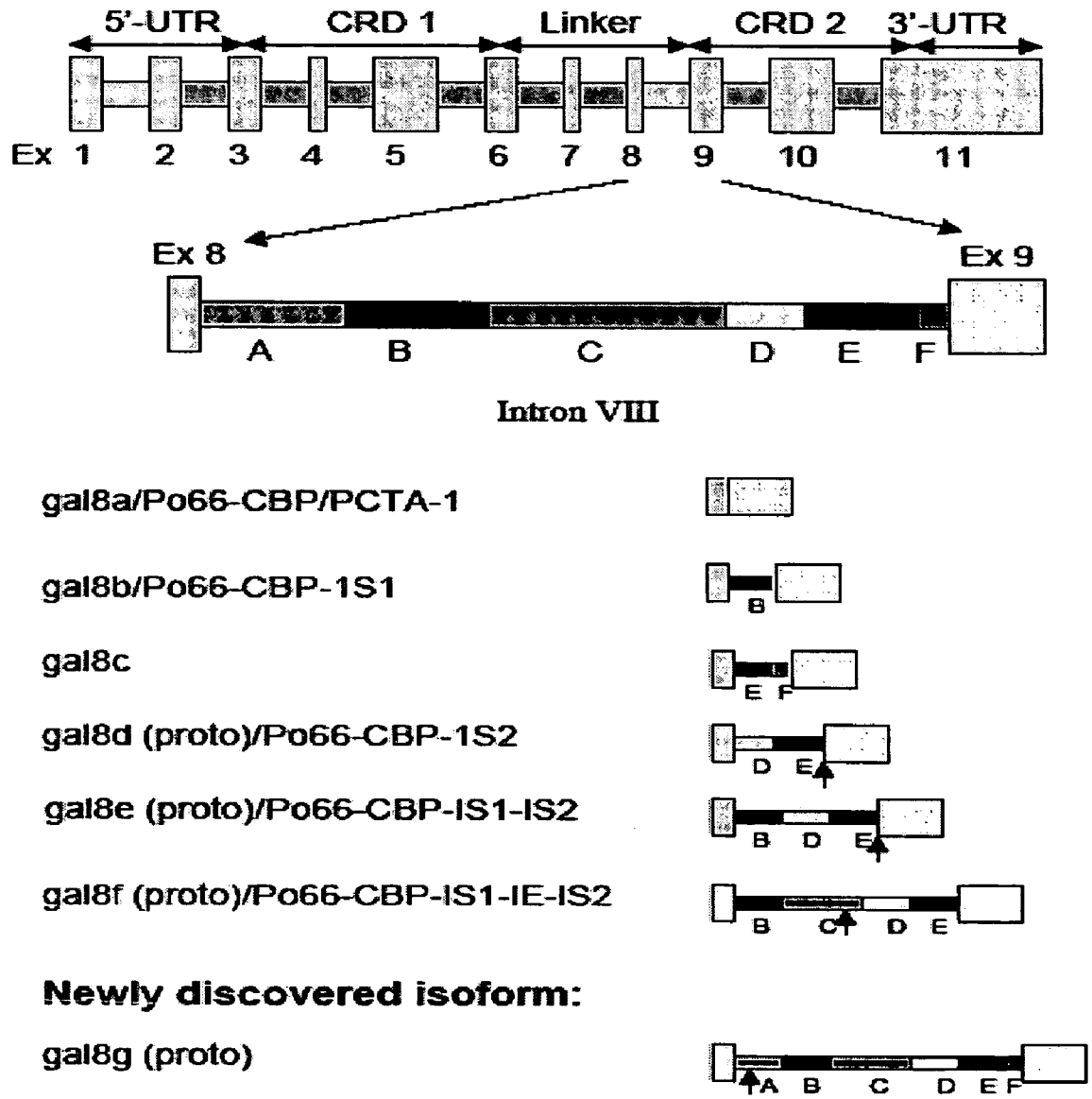
FIG. 3 shows gene organization of human gal8. Schematic representation of gal8 gene and cDNAs for several isoforms of gal8. Isoforms (three tandem-repeat type gal8a to gal8c and four proto type gal8d to gal8g) are produced by alternate splicing of intron VIII. The arrow in gal8d to gal8g indicates the stop codon. Alternative names for gal8 isoforms are based on Su et al. (1996) and Bidon et al. (2001).

Results relating to the assessment of gal8 expression in cancer cells are conflicting, but may be based on transcript heterogeneity. One study indicates that gal8, also known as prostate carcinoma tumor antigen-1 (PCTA-1; identified by surface-epitope masking and expression cloning) is selectively expressed in prostate cancer cells, but not in normal prostate or benign hyperplasia (Su et al., 1996). In contrast, gal8 has been reported as expressed at low levels in normal tissues as well as benign hyperplasia or adenocarcinoma by histochemistry (Danguy et al., 2001). This notion is supported by the results from Cancer Genome Anatomy Project (CGAP) library analysis (hyper text transfer protocol address cgap.nci.nih.gov/). The conflicting data on gal8 expression are most likely due to the complexity of gal8 structures, the diversity of isoforms as shown in FIG. 3, and the type of probes used in those studies. The gal8 gene encodes numerous mRNAs by alternate splicing mostly on intron VIII (Bidon et al., 2001). These mRNAs encode six different isoforms of gal8; three belong to the tandem-repeat type (containing two CRDs) and three to the proto type group (one CRD).

Figure 4:
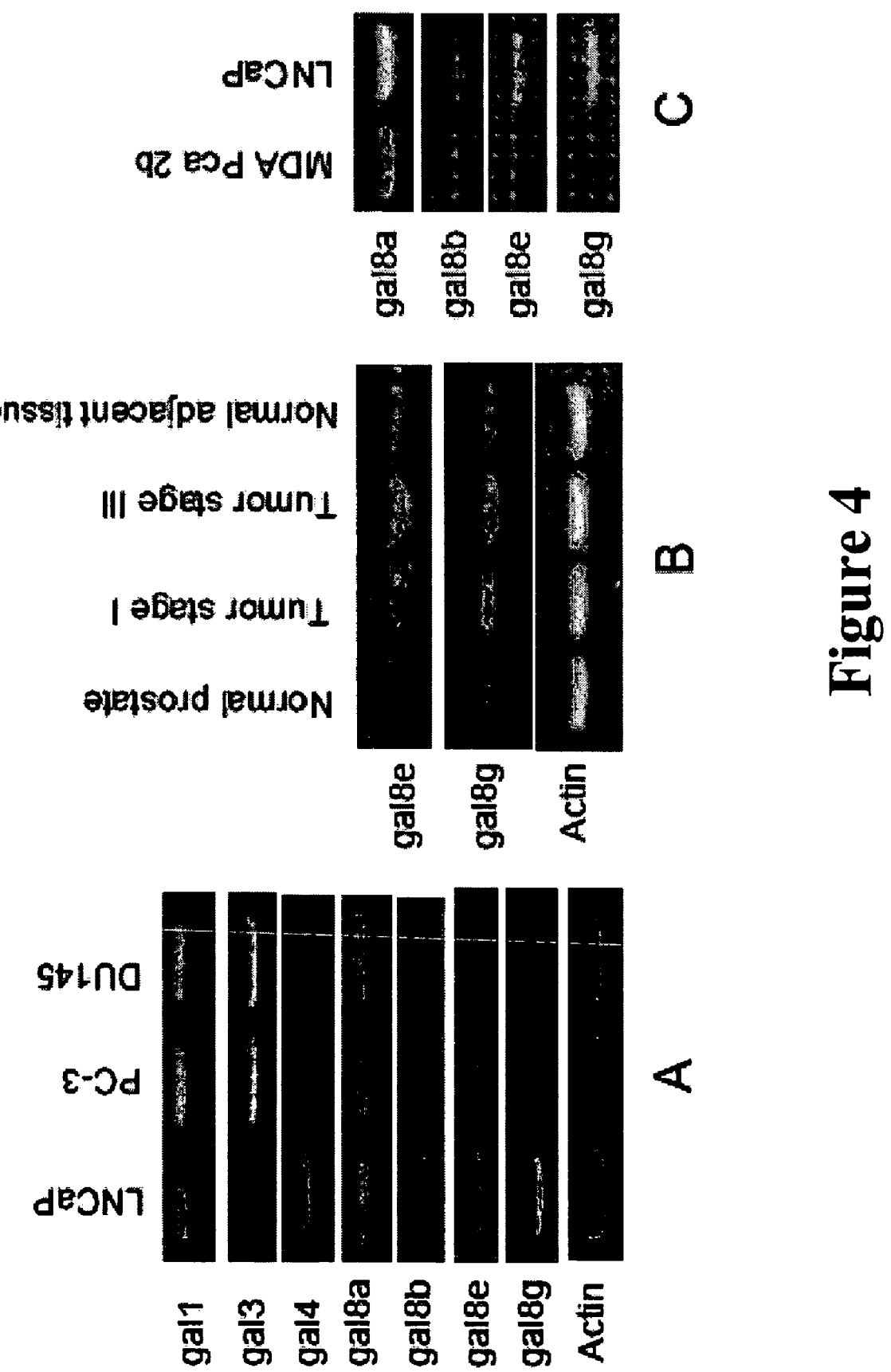
FIG. 4 shows results of RT-PCR analysis. Galectin expression in LNCaP, PC-3 and DU145 cell lines (A), prostate tissues (B), and MDA PCa 2b cell line (C).

A novel gal8 mRNA transcript has been discovered by the present inventors and discussed herein, which results in a distinct proto type isoform (gal8g) as shown in FIG. 3. Analysis of this transcript reveals a stop codon at the beginning of the spliced intron VIII, yielding a proto type isoform of gal8 (gal8g), which is different from all previously known proto gal8 isoforms (Bidon et al., 2001; Bidon-Wagner and Le Pennec J P, 2004). To confirm the authenticity of the gal8g, gene specific primers were designed from its non-overlapping sequence (beginning of the intron VIII, see FIG. 3) and a gene specific product was amplified from LNCaP cell and prostate tissues (see later). It was found that these high levels of expression of gal8g in the androgen dependent AD cell line LNCaP, but little or no expression in the androgen independent AI cell lines PC-3 and DU145, as shown in FIG. 4A.

DNA methylation is an enzyme-mediated chemical modification that adds methyl ($CH_3$) groups at selected sites of DNA. In mammals, DNA methylation is the only known natural modification of DNA and affects the cytosine (C) when it is followed by a guanosine (G). Thus, in mammals, DNA methylation occurs at CpG sites. In human, 70-80% of all CpG sites are methylated (See world wide web address: mdanderson.org). Epigenetic alterations including hypermethylation of gene promoters are proved to be early events in neoplastic progression (Hanahan and Weinberg, 2000; Warnecke and Bestor, 2000). Such alterations are believed to contribute to the neoplastic process by transcriptional silencing of tumor suppressor gene expression (Jones and Baylin, 2002). Thus, methylated genes can serve as biomarkers for early detection of cancer (Fackler et al., 2004).

Abnormal gal1 expression has been found during cell dedifferentiation, and in neoplastic cells. A small genomic region of approximately 100 base pairs surrounding the transcriptional start site (−50/+50) accounts for most transcriptional activity of gal1 (Salvatore et al., 1998). Using the bisulfite genomic sequencing technique (bisulfite converts unmethylated C to U), it was found that the mechanism that mainly controls the cell-specific expression and the reactivation of gal1 gene is the transition from a fully methylated to a fully unmethylated state of 11 CpG sites near the transcription start site (Benvenuto et al., 1996). Also, in normal mouse and rat tissues the rate of DNA methylation of the small CpG island surrounding the start correlates with transcription activity (Salvatore et al., 1998). Recently, Kondoh et al. (2003) demonstrated that the activation of gal1 gene in human hepatocellular carcinoma involves methylation-sensitive complex formations at the transcriptional upstream and downstream elements. The gal3 start site lies in the middle of a large CpG island and thus DNA methylation could be one of the mechanisms governing gal3 gene expression (Chiariotti et al., 1999). The expression of gal3 gene was found silenced by methylation of its promoter in murine melanoma cells (Costa et al., 2003). However, similar gene silencing mechanisms for gal8 by promoter methylation was heretofore unknown.

To determine levels of expression in different cells and tissues, expression of gal1, 3, 4, and 8 was characterized in PC cells and prostate tissues (normal and tumor) by RT-PCR. Gal1 was expressed in all PC cells tested as shown in FIG. 4A. Gal3 was highly expressed in the AI cell lines PC-3 and DU145, but weakly expressed in the AD cell line LNCaP. Expression of gal4 in LNCaP was intense, but weak in both PC-3 and DU145. Expression of gal8 isoforms is intriguing: the newly discovered proto isoform gal8g is highly expressed in LNCaP, but not expressed in either PC-3 or DU145. Similar results were obtained with gal8b (also known as Po66-CBP-IS1) and gal8e (also known as Po66-CBP-IS1-IS2). However, gal8a (also known as PCTA-1 and Po66-CBP) is equally expressed in all three cell lines. The other gal8 isoforms (gal8c, gal8d, and gal8f) were not detected in the RT-PCR studies.

Normal and tumor prostate tissues (RNAs obtained from Ambion, Austin, Tex.) were analyzed by RT-PCR for galectin expression and the results shown in FIG. 4B. The expression of either gal8e or gal8g in stage III tumor (T3N0M0, grading and tumor staging according to the 1997 UICC classification) was higher than that in stage I (T1N0M0), although expression in both tumor cell types was still higher than that in normal prostate or normal adjacent tissue.

It is noteworthy that another AD PC cell line, MDA PCa 2b, which originates in a bone metastasis, shows expression of gal8a similar to LNCaP; but unlike LNCaP, it shows little or no expression of gal8b, gal8e, and gal8g as shown in FIG. 4C.

These results indicate that expression of galectins in PC cells does not correlate with their AD properties, but rather relate to their aggressiveness (non-metastatic versus metastatic).

Figure 5:
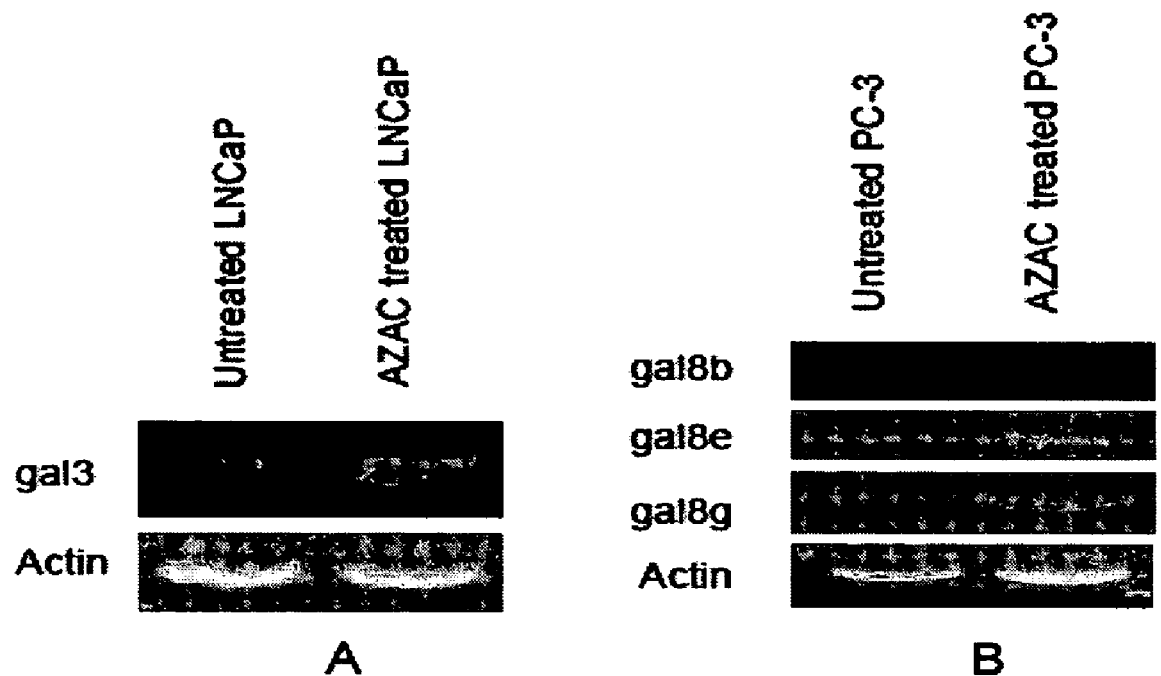
FIG. 5 shows expression of gal3 in azacytidine-treated LNCaP (A) and gal8 isoforms in azacytidine-treated PC-3 cells (B).

As shown in FIG. 4A, the gal3 gene is silent in LNCaP. In contrast, most gal8 isoforms except gal8a are silent in PC-3 and DU145. The present inventors determined that DNA methylation of galectin genes is responsible for gene silencing. Since azacytidine blocks cytidine methyl transferase activity, treatment of cells with azacytidine should reactivate the genes. Treatment of LNCaP and PC-3 cells was accomplished by adding 10 uM 5-aza-2'-deoxycytidine daily for five days to the culture medium. RT-PCR was then performed on RNA extracted from the treated PC cells. Azacytidine-treated LNCaP showed expression of gal3 as shown in FIG. 5A. Similarly, AZAC-treated PC-3 showed expression of gal8b, gal8e, gal8g by RT-PCR as shown in FIG. 5B. These results indicate that gal3 and gal8 promoters may be methylated in LNCaP and PC-3 cells, respectively.

Figure 6:
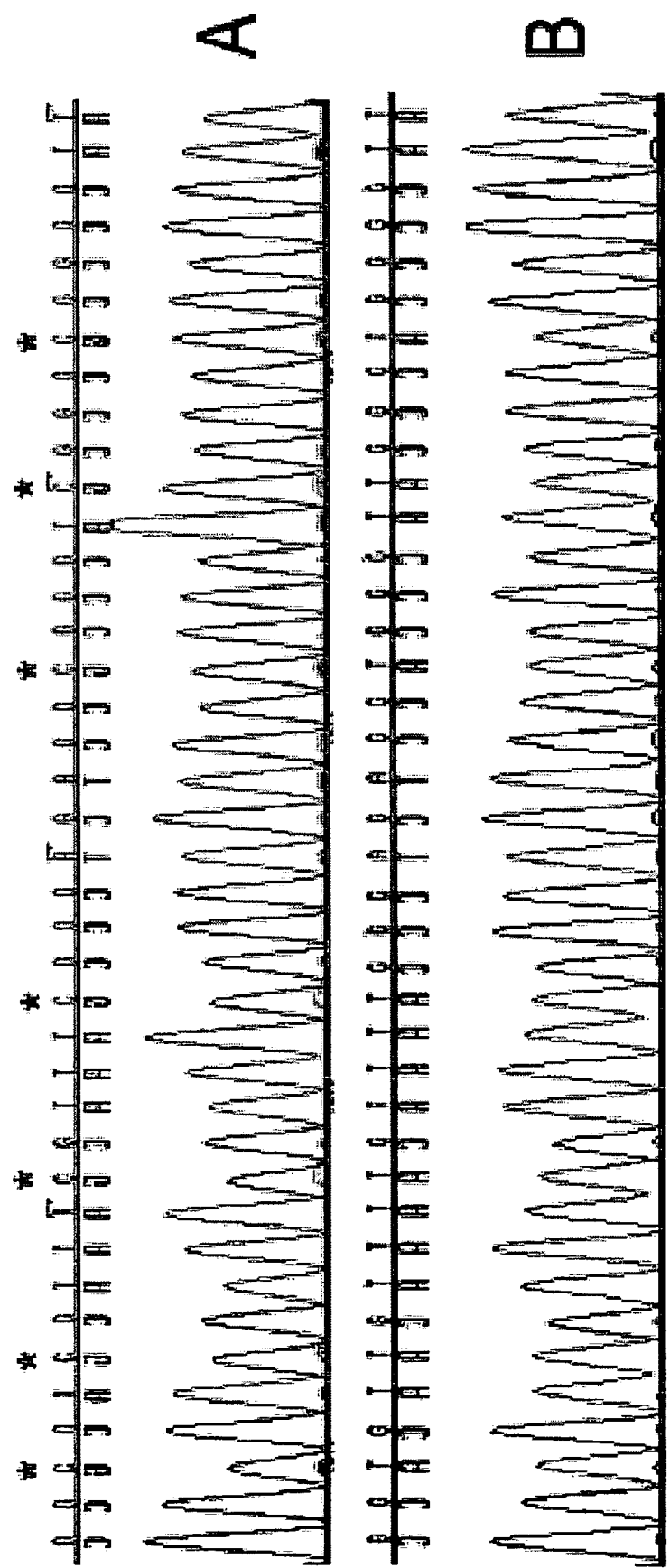
FIG. 6 shows sequencing chromatogram of bisulfite treated DNA. A. Partial chromatogram showing cytosine methylation (indicated by asterics) of the gal3 promoter in LNCaP. The sequence shows two CpG islands (−73 to −34 nt) (Kadrofske et al., 1998). B. The gal3 promoter sequence is either from PC-3 or DU 145 or human placenta. Note that all nucleotides (in B) corresponding to the methylated C (in A) have changed to T, which represents U in the promoter.

Bisulfite genomic sequencing allows precise analysis of methylation in a certain region by converting all non-methylated cytosines (C) into uracil (U) by bisulfite treatment, while methylated cytosines remain unchanged. Cytosine deamination by bisulfite treatment of single-stranded DNA and subsequent PCR amplification (CD-PCR) was performed as previously described (Frommer et al., 1992). DNA was obtained from LNCaP, PC-3, and DU145 cell lines using Quiak DNAEasy extraction kit (Qiagen, Valencia, Calif.), and bisulfite reaction was carried out on 2 ug of genomic DNA. A PCR-amplified product of the gal3 promoter was obtained using the primer pairs constructed after taking into account the bisulfite conversion reaction. About 50 cytosines in gal3 promoter were found methylated in 400 bp long amplified product as shown in FIG. 6.

Figure 7:
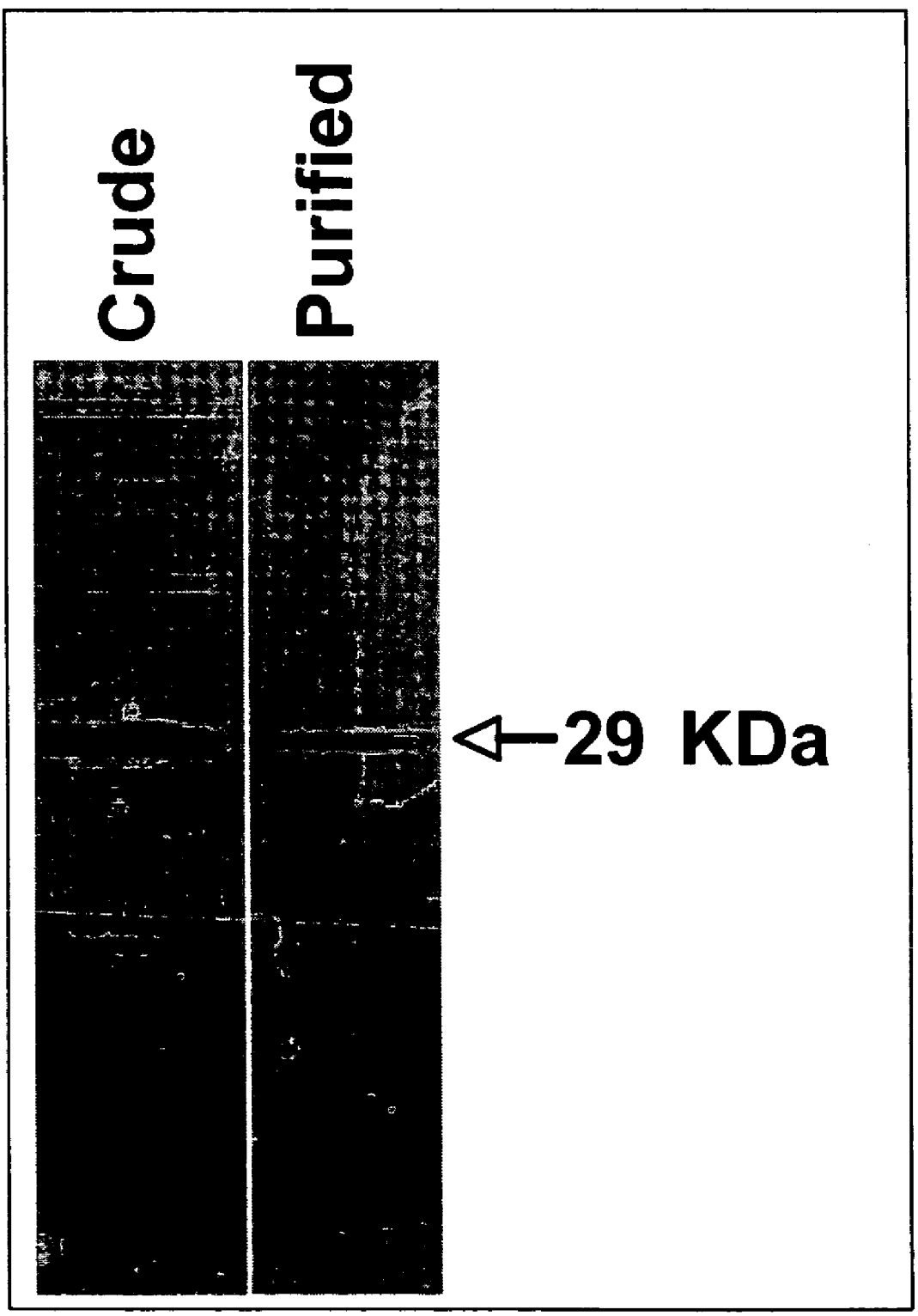
FIG. 7 shows a blot of purification of human recombinant gal3. 15% SDS-PAGE of the lactosyl-Sepharose purified gal3.
Figure 8:
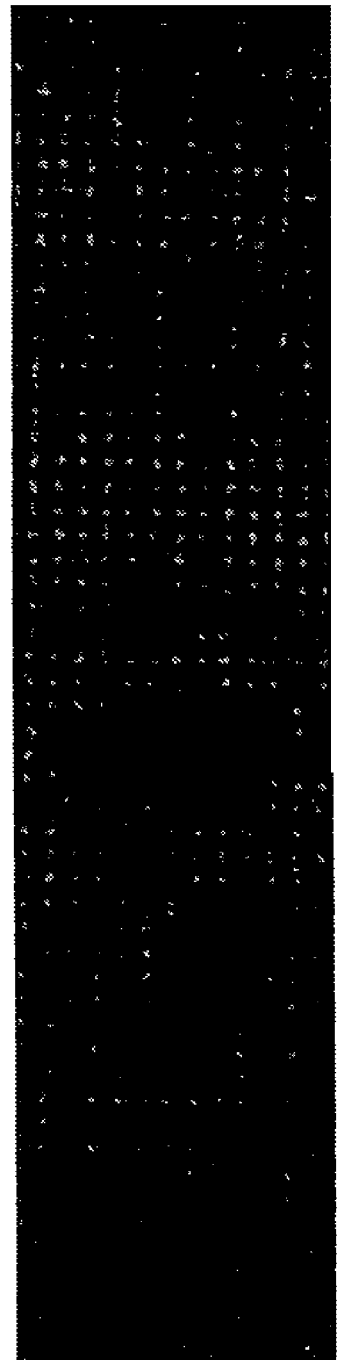
FIG. 8 is a blot showing the specificity of anti-gal3 antibodies. Crude cell extract (MC3T3E1) was tested with the anti-galectin-3 antibodies on western blot.

Human gal3 recombinant protein was expressed in *E. coli* from a construct placed into the pET vector (Novagen, Madison, Wis.). The recombinant galectin was purified on a lactosyl-Sepharose column as shown in FIG. 7. Gal8a and gal8g were also cloned into pET vector for recombinant expression of the tandem-repeat and proto type proteins, respectively. The purified recombinant gal3 and gal8a are used to raise antibodies and used as antigens in immunoassays. Specifically, the purified recombinant gal3 was used to raise antibodies in rabbits (Duncroft, Lovettsville, Md.). The antiserum titer was determined by ELISA as previously described (Ahmed et al., 2004), and its specificity assessed by western blot of MC3T3E1 (mouse calvaria-derived osteoblasts) cell extract as shown in FIG. 8. This antibody can be used for immunostaining of gal3 in normal and tumor tissues as well as in immunoassay and western blot to identify gal3 in sera from healthy individuals and prostate cancer patients. In order to generate specific antibodies against gal8g, a non-overlapping peptide not encoded by any other known gal8 variant (beginning of spliced intron VIII, see FIG. 3) is used to immunize rabbits.

PCR products specific for gal3 and gal8g (non-overlapping oligonucleotides not encoded by any other known gal8 variant, at the beginning of spliced intron VIII, see FIG. 3) were cloned into a pGEM-T vector (Promega, Madison, Wis.) and linearized by restriction digest with either SacII or SpeI. Antisense and sense RNA probes were synthesized by incorporating digoxigenin-UTP (Roche, Indianapolis, Ind.) using T7 and SP6 RNA polymerase (Promega) as previously described (Ahmed et al., 2004).

The rigorous characterization of the galectin expression in various stages of prostate cancer tissues, normal prostate tissues, and BPH tissues is critical for development of biological markers for diagnosis and prognosis of prostate cancer, thus expression of gal3 and gal8 is investigated in normal and tumor prostate tissues by RT-PCR, Northern analysis, western blot, and quantitative real time PCR. Biopsy samples from various stages of tumors (RNAs are commercially available from Ambion, Austin, Tex.) are examined for galectin expression by RT-PCR and quantitative real time PCR. Normal and tumor prostate tissues and BPH tissues (using slides that are commercially available from TeleChem International, Inc., Sunnyvale, Calif.) are examined for in situ hybridization and immunostaining. It is known that galectins are secreted to serum (Iurisci et al., 2000) and these galectins in sera from healthy human and prostate cancer patients is examined by westernblot and immunoassays. For immunostaining, antibodies are raised against selected galectins, preferably gal3 and gal8g. Recombinant galectins will be expressed into *E. coli*. In order to generate gal8g specific antibodies, non-overlapping peptides are used.

EXAMPLES

Materials and Methods

RT-PCR is performed on tissue RNAs (available from Ambion) using the Reverse Transcription System (Promega, Madison, Wis.) following the manufacturer's instructions. For expression of gal3 and gal8g genes, custom primers specific to each galectin are made by Invitrogen (Carlsbad, Calif.). For RNA integrity and loading control, β-actin is used and amplified. PCR is performed in a PTC-200 thermal cycler from MJ research (Waltham, Mass.) using the protocols previously described (Ahmed et al., 2004).

As discussed above, results show a distinct expression pattern of galectins in PC cells. Most notably, gal3 is highly expressed in AI cell lines PC-3 and DU145, but show little or no expression in AD cell line LNCaP as shown in FIG. 4A. In contrast, most isoforms of gal8 are expressed in LNCaP, but exhibit little or no expression in PC-3 and DU145

Total RNA (20 ug) is resolved in a 1% agarose/6% formaldehyde gel, transferred to nylon membranes and probed for various galectins. The gene specific DNA probes are prepared by random-primed reactions using partial or complete coding sequence of galectin cDNA.

In situ hybridization and immunostaining is carried out following the protocols previously described (Ahmed et al., 2004). Antisense and sense probes have been developed for gal3 and gal8g for in situ hybridization. Specific anti-gal3 antibodies have been developed to be used for immunostaining. Biopsy slides, each containing about 84 spots of various stages of prostate cancer, BPH, PIN, and normal prostate, are purchased from TeleChem International, Inc. (Sunnyvale, Calif.). Moreover, tissues of various stages of prostate tumor are obtained from the Cooperative Human Tissue Network (National Cancer Institute) and the Western Pennsylvania prostate Tissue Bank (Applications in process).

In PC cell lines, cytosine methylation represses the glutathione S-transferase P1 gene (Singal et al., 2001). In the present invention, gal3 was highly expressed in PC-3 and DU145, but showed little or no expression in LNCaP. In contrast, several galectin-8 isoforms were found in LNCaP, but with little or no expression in PC-3 and DU145 (see FIG. 4). However, azacytidine-treated LNCaP and PC-3 cells showed expression of gal3 and gal8 isoforms, respectively (see FIG. 5). Azacytidine blocks cytidine methyltransferase activity.

To determine the level of methylation, cytosine deamination of single-stranded DNA by bisulfite treatment is performed. Genomic DNA from normal prostate and tumor prostate tissues is purchased from Ambion (Austin, Tex.).

Genomic DNA from human placenta (Sigma) is used as a control. Genomic DNA (8 ug) is digested with XbaI and then denatured in 0.3 M NaOH for 15 min at 37° C. in a volume of 100 ul, and then 60 ul of 10 mM hydroquinone and 1.04 ml of 3.6 M sodium bisulfite (pH 5) is added. The reaction mixture is incubated at 50° C. for 16 h in the dark. The DNA is purified with a desalting column (Magic DNA Clean-Up System; Promega), denatured with 0.3 M NaOH for 15 min at 37° C., neutralized with 3 M ammonium acetate (pH 7), and ethanol precipitated. An aliquot of DNA is amplified by using modified primers (see below). All PCRs is carried out in 50-ul volumes containing 10 mM Tris, 50 mM KCl, 3 mM $MgCl_2$, 5% dimethyl sulfoxide, 0.2 mM deoxynucleoside triphosphates, 5 pmol of each primer, and 1 U of Taq polymerase (Stratagene) as previously described (Ahmed et al., 2004). The amplified fragments are cloned into the pCRII vector of the TA cloning system (Invitrogen), and at least 20 independent clones for each fragment are sequenced by using T7 primer (Novagen) to determine the methylation pattern. The primers for gal3 after taking into account the bisulfite conversion reaction are: (a) forward primer (HuG3BPF1), 5'-TAAGGTGGAAGTGGTAAGGGG-3' (SEQ ID NO: 1) derived from the wild-type sequence 5-CAAGGTG-GAAGTGGCAAGGGG-3' (SEQ ID NO: 2); and (b) reverse primer (HuG3BPR1), 5'-CCCCACACAACTCACCACTC-3' (SEQ ID NO: 3) derived from the wild-type sequence 5'-CCCCGCGCAGCTCACCGCTC-3' (SEQ ID NO: 4). The primers are chosen from the area outside the CpG islands. Similarly, primers for methylated and unmethylated gal8 promoter are made and PCR amplification is performed. Cytosine methylation is shown in gal3 promoter in LNCaP. Various degree of methylation of gal3 and gal8 promoters are shown in various stages of prostate cancer.

It was found that gal3 and gal8g are differentially expressed in various stages of prostate cancer as shown in Table 1. Expression of gal3 is dramatically decreased in stage II PC relative to the normal tissue, and although its expression is slightly increased in stage III PC, it is still lower than normal (Pacis et al., 2000). In contrast, gal8 is highly expressed in PC, but not in normal prostate or BPH (Su et al., 1996). Results of differential expression of galectins and cytosine methylation of their promoters in various stages of PC are the basis of this described differential assay. Further, because Galectins are secretory and are found in serum and body fluids (Su et al., 1996; Iurisci et al., 2000), these body fluids constitute an ideal target for the development of diagnostic assays for PC. Furthermore, reliable semi- or quantitative methods for assessing levels of these markers in urine constitutes the ideal non-invasive methods for PC diagnosis to be applied at the doctor's office.

Figure 9:
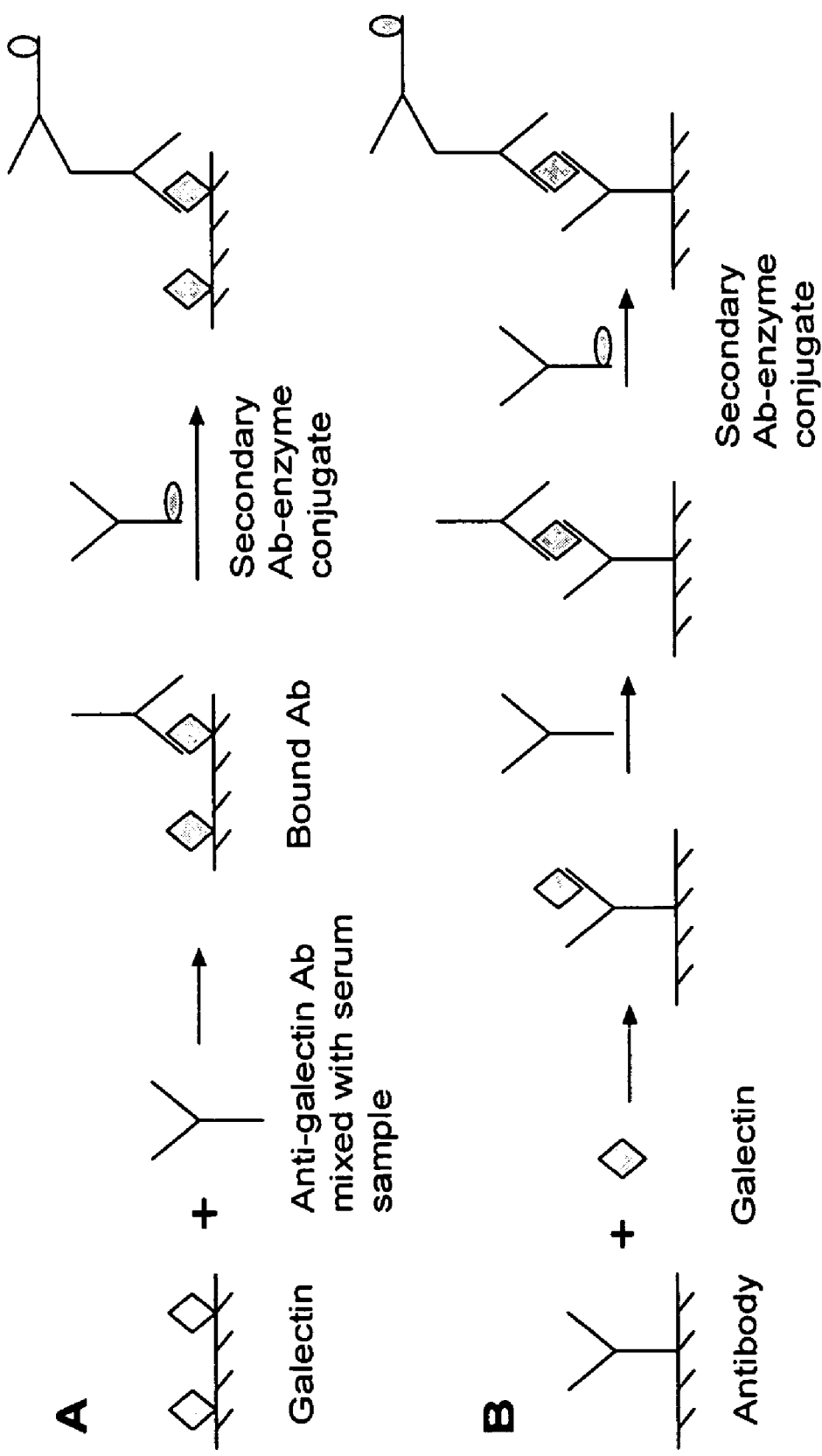
FIG. 9 is a schematic representation of immunoassay.

Solid phase immunoassays are used for quantitation of gal3, gal8a, and gal8g in biological samples. The presence of galectins in sera is examined by immunoassays as shown in FIG. 9A. In the immunoassay, the galectin is coated on a 96-well plate and the known amount of anti-galectin antibody (anti-gal3 or anti-gal8g) is pre-mixed with varying amount of standard antigen (galectin) or unknown sample (serum) and added to plate. The amount of galectin in the serum is measured from a standard curve. Alternatively, anti-galectin antibodies are coated and serum (or standard galectin) is added onto the wells, and the bound galectin is quantitated with the anti-galectin antibodies followed by secondary antibody conjugated to horseradish peroxidase as described elsewhere (Iurisci et al., 2000) and shown in FIG. 9B.

Figure 10:
FIG. 10 is a schematic representation of MS-PCR illustrating reactions using methylated DNA (SEQ ID NO: 5) or unmethlyated DNA (SEQ ID NO: 6) and primers (SEQ ID NOs: 7 and 8).

MS-PCR is performed to assess the methylation status of a particular group of CpG sites within a CpG island. The procedure entails initial modification of DNA by sodium bisulfite and subsequent amplification with primers specific for methylated (M primer) versus unmethylated (U primer) DNA (Herman et al., 1996). The difference between the CD-PCR described above and MS-PCR is that the location of primer site. In CD-PCR, primers are designed from the regions outside the CpG islands and the methylation status of the CpG islands is investigated from cloning and sequencing of the PCR product. In MS-PCR, primers are chosen from the CpG sites to discriminate between methylated and unmethylated alleles following bisulfite treatment and thus the methylation status of the CpG islands is assessed directly from the PCR product. The PCR product is expected only in tubes where methylated DNA is mixed with the M primer and unmethylated DNA is mixed with U primer (see FIG. 10 illustrating exemplary sequences SEQ ID NO: 5 (methylated DNA modified by sodium bisulfite), SEQ ID NO: 6 (unmethylated DNA modified by sodium bisulfite), SEQ ID NO: 7 (U primer), and SEQ ID NO: 8 (M primer)). PCR amplification of modified or unmodified DNA with the primers specific for methylated or unmethylated DNA is achieved as described above.

Abbreviations

As used herein, the following abbreviations have the meanings set forth below.

PC: prostate carcinoma;
DRE: digital rectum examination;
PSA: prostate specific antigen;
gal3: galectin-3;
gal8: galectin-8;
NHD: New Horizon Diagnostics Corp. (Columbia, Md.);
BPH: benign prostatic hyperplasia;
PIN: prostatic intraepithelial neoplasia;
AZAC: azacytidine;
MS-PCR: methylation-specific PCR;
AD: androgen-dependent; and
AI: androgen-independent.

BIBLIOGRAPHY

The contents of all cited references are incorporated herein by reference for all purposes.

Ahmed H, Allen H J, Sharma A, Matta K L. Human splenic galaptin: carbohydrate-binding specificity and characterization of the combining site. Biochemistry 1990; 29:5315-9.

Ahmed H, Sharma A, DiCioccio R A, Allen H J. Lymphoblastoid cell adhesion mediated by a dimeric and polymeric endogenous beta-galactoside-binding lectin (Galaptin) J Mol Recognition. 1992; 5:1-8.

Ahmed H, Fink N E, Vasta G R. A novel solid-phase assay for lectin binding: comparative studies on beta-galactoside-binding S-type lectins from fish, amphibian, and mammalian tissues. Ann N Y Acad Sci. 1994a; 712:315-317.

Ahmed H, Fink N E, Vasta G R. Elasmobranch and teleost fish contain thiol-dependent β-galactoside binding lectins that cross-reactive with those identified and characterized in bovine spleen. Ann N Y Acad Sci. 1994b; 712:318-20.

Ahmed H, Vasta G R. Galectins: conservation of functionally and structurally relevant amino acid residues defines two types of carbohydrate recognition domains. Glycobiology 1994; 4:545-9.

Ahmed H, Fink N E, Pohl J, Vasta G R. Galectin-1 from bovine spleen: Biochemical characterization, carbohydrate specificity and tissue-specific isoform profiles. J. Biochem (Tokyo). 1996a; 120:1007-19.

Ahmed H, Pohl J, Fink N E, Strobel F, Vasta G R. The primary structure and carbohydrate specificity of a β-galactosyl-binding lectin from toad (*Bufo arenarum* Hensel) ovary reveal closer similarities to the mammalian galectin-1 than to the galectin from the clawed frog *Xenopus laevis*. J Biol Chem. 1996b; 271:33083-94.

Ahmed H, Bianchet M A, Amzel L M, Hirabayashi J, Kasai K, Giga-Hama Y, Tohda H, Vasta G R. Novel carbohydrate specificity of the 16 kDa galectin from *Caenorhabditis elegans*: Binding to blood group precursor oligosaccharides (type 1, type 2, $T_\alpha$, and $T_\beta$) and gangliosides. Glycobiology 2002; 12:451-61.

Ahmed H, Du S J, O'Leary N, Vasta, G R. Biochemical and molecular characterization of galectins from zebrafish (*Danio rerio*). Notochord-specific expression of a proto type galectin (Drgal1-L2) during early embryogenesis. Glycobiology 2004; 14:219-32.

Akahani S, Nangia-Makker P, Inohara H, Kim H R, Raz A. Galectin-3: a novel antiapoptotic molecule with a functional BH1 (NWGR) domain of Bcl-2 family. Cancer Res. 1997; 57:5272-6.

Allen H J, Sharma A, Ahmed H, Piver M S, Gamarra M. Galaptin and galaptin-binding glycoconjugates in serum and effusions of carcinoma patients. Tumour Biol. 1993; 14:360-8.

Avni O, Pur Z, Yefenof E, Baniyash M. Complement receptor 3 of macrophages is associated with galectin-1-like protein. J Immunol. 1998; 160:6151-8.

Barondes S H, Cooper D N W, Gitt M A, Leffler H. Galectins. Structure and function of a large family of animal lectins. J Biol Chem. 1994; 269:20807-10.

Benvenuto G, Carpentieri M L, Salvatore P, Cindolo L, Bruni C B, Chiariotti L Cell-specific transcriptional regulation and reactivation of galectin-1 gene expression are controlled by DNA methylation of the promoter region. Mol Cell Biol. 1996; 16:2736-43. Erratum in: Mol Cell Biol. 1996; 16:4590

Bianchet, M. A., Ahmed, H., Vasta, G. R., Amzel, L. M. A soluble β-galactosyl-binding lectin (galectin) from toad (*Bufo arenarum* Hensel) ovary: Crystallographic studies of two protein-sugar complexes. Proteins 2000; 40:378-88.

Bidon N, Brichory F, Hanash S, Bourguet P, Dazord L, Le Pennec J P. Two messenger RNAs and five isoforms for Po66-CBP, a galectin-8 homolog in a human lung carcinoma cell line. Gene. 2001 Aug. 22; 274:253-62.

Bidon-Wagner N, Le Pennec J P. Human galectin-8 isoforms and cancer. Glycoconj J. 2004; 19:557-63.

Califice S, Castronovo V, Bracke M, van den Brule F. Dual activities of galectin-3 in human prostate cancer: tumor suppression of nuclear galectin-3 vs tumor promotion of cytoplasmic galectin-3. Oncogene. 2004; 23:7527-36.

Camby I, Belot N, Rorive S, Lefranc F, Maurage C A, Lahm H, Kaltner H, Hadari Y, Ruchoux M M, Brotchi J, Zick Y, Salmon I, Gabius H J, Kiss R. Galectins are differentially expressed in supratentorial pilocytic astrocytomas, astrocytomas, anaplastic astrocytomas and glioblastomas, and significantly modulate tumor astrocyte migration. Brain Pathol. 2001; 11: 12-26.

Caplan A and Kratz A. Prostate-specific antigen and the early diagnosis of prostate cancer. Am J Clin Pathol 2002; 117: S104-8

Chiariotti L, Salvatore P, Benvenuto G, Bruni C B. Control of galectin gene expression. Biochimie. 1999; 81:381-8.

Cho M, Cummings R D. Galectin-1, a β-galactoside-binding lectin in Chinese hamster ovary cells. II. Localization and biosynthesis. J Biol Chem. 1995; 270:5207-12.

Colnot C, Ripoche M, Fowlis D, Cannon V, Scaerou F, Cooper D N W, Poirier F. The role of galectins in mouse development. Trends Glycosci Glycotechnol. 1997; 9:31-40.

Colnot C, Sidhu S S, Balmain N, Poirier F. Uncoupling of chondrocytes death and vascular invasion in mouse galectin 3 null mutant bones. Dev Biol. 2001; 229:203-14.

Cooper D N W. Galectinomics: a lesson in complexity. Biochim Biophys Acta 2002; 1572:209-31.

Cooper D N W, Barondes S H. Evidence for export of a muscle lectin from cytosol to extracellular matrix and for a novel secretory mechanism. J Cell Biol. 1990; 110: 1681-91.

Cooper D N W, Massa S M, Barondes S H. Endogenous muscle lectin inhibits myoblast adhesion to laminin. J Cell Biol. 1991; 115:1437-48.

Costa M, Teixeira, V R, Junqueira M S, Costa F F, Camargo A A, Chammas R.; Galectin-3 gene expression is silenced by methylation of its promoter in murine melanoma cells. 1° Simpósio Avanços em Pesquisas Médicas dos Laboratórios de Investigação Médica do HC-FMUSP, 2003, São Paulo, 2003; Abstract R256.

Danguy A, Rorive S, Decaestecker C, Bronckart Y, Kaltner H, Hadari Y R, Goren R, Zich Y, Petein M, Salmon I, Gabius H J, Kiss R. Immunohistochemical profile of galectin-8 expression in benign and malignant tumors of epithelial, mesenchymatous and adipous origins, and of the nervous system. Histol Histopathol. 2001; 16:861-8.

Ellerhorst J, Nguyen T, Cooper D N, Lotan D, Lotan R. Differential expression of endogenous galectin-1 and galectin-3 in human prostate cancer cell lines and effects of overexpressing galectin-1 on cell phenotype. Int J Oncol. 1999a; 14:217-24.

Ellerhorst J, Troncoso P, Xu X C, Lee J, Lotan R. Galectin-1 and galectin-3 expression in human prostate tissue and prostate cancer. Urol Res. 1999b; 27:362-7.

Fackler M J, McVeigh M, Mehrotra J, Blum M A, Lange J, Lapides A, Garrett E, Argani P, Sukumar S. Quantitative multiplex methylation-specific PCR assay for the detection of promoter hypermethylation in multiple genes in breast cancer: Cancer Res., 64(13):4442-52 (2004).

Frommer M, McDonald L E, Millar D S, Collis C M, Watt F, Grigg G W, Molloy P L, Paul C L. A genomic sequencing protocol that yields a positive display of 5-methylcytosine residues in individual DNA strands. Proc Natl Acad Sci USA. 1992; 89:1827-31.

Gauthier L, Rossi B, Roux F, Termine E, Schiff C. Galectin-1 is a stromal cell ligand of the pre-B cell receptor (BCR) implicated in synapse formation between pre-B and stromal cells and in pre-BCR triggering. Proc Natl Acad Sci USA. 2002; 99:13014-9.

Gibson U E, Heid C A, Williams P M. A novel method for real time quantitative PCR. Genome Res. 1996; 6:986-94.

Glinsky V V, Glinsky G V, Rittenhouse-Olson K, Huflejt M E, Glinskii O V, Deutscher S L, Quinn T P. The role of Thomsen-Friedenreich antigen in adhesion of human breast and prostate cancer cells to the endothelium. Cancer Res. 2001; 61:4851-7.

Glinsky V V, Huflejt M E, Glinsky G V, Deutscher S L, Quinn T P. Effects of Thomsen-Friedenreich antigen-specific peptide P-30 on beta-galactoside-mediated homotypic aggregation and adhesion to the endothelium of MDA-MB-435 human breast carcinoma cells. Cancer Res. 2000; 60:2584-8.

Goletz S, Hanisch F G, Karsten U. Novel alphaGalNAc containing glycans on cytokeratins are recognized invitro by galectins with type II carbohydrate recognition domains. J Cell Sci. 1997; 110:1585-96.

Gong H C, Honjo Y, Nangia-Makker P, Hogan V, Mazurak N, Bresalier R S, Raz A. The NH2 terminus of galectin-3 governs cellular compartmentalization and functions in cancer cells. Cancer Res. 1999; 59:6239-45.

Gotz W, Kasper M, Miosge N, Hughes R C. Detection and distribution of the carbohydrate binding protein galectin-3 in human notochord, invertebral disc and chordoma. Differentiation 1997; 62:149-57.

Gu M, Wang W, Song W K, Cooper D N, Kaufman S J. Selective modulation of the interaction of alpha 7 beta 1 integrin with fibronectin and laminin by L-14 lectin during skeletal muscle differentiation. J Cell Sci. 1994; 107:175-81.

Hadari Y R, Arbel-Goren R, Levy Y, Amsterdam A, Alon R, Zakut R, Zick Y. Galectin-8 binding to integrins inhibits cell adhesion and induces apoptosis. J Cell Sci. 2000; 113: 2385-97.

Hanahan D, Weinberg R A. The hallmarks of cancer. Cell 2000: 100:57-70.

Herman J G, Graff J R, Myohanen S, Nelkin B D, Baylin S B. Methylation-specific PCR: A novel PCR assay for methylation status of CpG islands. Proc Natl Acad Sci USA 1996; 93:9821-6.

Hernandez J D, Baum L G. Ah, sweet mystery of death! Galectins and control of fate. Glycobiology 2002; 12:127R-136R Hirabayashi J, Kasai K. The family of metazoan metal-independent β-galactoside-binding lectins:structure, function and molecular evolution. Glycobiology 1993; 3:297-304.

Inohara H, Raz A. Functional evidence that cell surface galectin-3 mediates homotypic cell adhesion. Cancer Res. 1995; 55:3267-71.

Iurisci I, Tinari N, Natoli C, Angelucci D, Cianchetti E, Iacobelli S. Concentrations of galectin-3 in the sera of normal controls and cancer patients. Clin Cancer Res. 2000; 6:1389-93.

Jain S, Bhojwani A G, Mellon J K. Improving the utility of prostate specific antigen (PSA) in the diagnosis of prostate cancer: the use of PSA derivatives and novel markers. Postgrad Med J. 2002; 78:646-50

Jones P A, Baylin S B. The fundamental role of epigenetic events in cancer. Nat Rev Genet. 2002; 3:415-28.

Kadrofske M M, Openo K P, Wang J L. The human LGALS3 (galectin-3) gene: determination of the gene structure and functional characterization of the promoter. Arch Biochem Biophys. 1998; 349:7-20.

Keetch D W, Catalona W J, Smith D S. Serial prostatic biopsies in men with persistently elevated serum prostate specific antigen values. J Urol. 1994; 151:1571-4.

Kondoh N, Hada A, Ryo A, Shuda M, Arai M, Matsubara O, Kimura F, Wakatsuki T, Yamamoto M. Activation of Galectin-1 gene in human hepatocellular carcinoma involves methylation-sensitive complex formations at the transcriptional upstream and downstream elements. Int J Oncol. 2003; 23:1575-83.

Leffler H, Barondes S H. Specificity of binding of three soluble rat lung lectins to substituted and unsubstituted mammalian β-galactosides. J Biol Chem. 1986; 261:10119-26.

Leffler H, Carlsson S, Hedlund M, Qian Y, Poirier F. Introduction to galectins. Glycoconj J. 2004; 19:433-40.

Levy Y, Arbel-Goren R, Hadari Y R, Eshhar S, Ronen D, Elhanany E, Geiger B, Zick Y. Galectin-8 functions as a matricellular modulator of cell adhesion. J Biol Chem. 2001; 276:31285-95.

Liao D I, Kapadia G, Ahmed H, Vasta G R, Herzberg O. Structure of S-lectin, a developmentally regulated vertebrate beta-galactoside binding protein. Proc Natl Acad Sci USA. 1994; 91:1428-32.

Liu F-T. Galectins: a new family of regulators of inflammation. Clin. Immunol. 2000; 97:79-88.

Liu F T, Rabinovich G A. Galectins as modulators of tumour progression. Nat Rev Cancer. 2005; 5:29-41.

Matarrese P, Fusco O, Tinari N, Natoli C, Liu F T, Semeraro M L, Malomi W, Iacobelli S. Galectin-3 overexpression protects from apoptosis by improving cell adhesion properties. Int J Cancer. 2000; 85:545-54.

Mizejewski, G. Role of integrins in cancer: Survey of expression patterns. Proc Soc Exp Biol Med. 1999; 222:124-38.

Nangia-Makker P, Conklin J, Hogan V, Raz A. Carbohydrate-binding proteins in cancer, and their ligands as therapeutic agents. Trends Mol Med. 2002; 8:187-92.

Nangia-Makker P, Honjo Y, Sarvis R, Akahani S, Hogan V, Pienta K J, Raz A. Galectin-3 induces endothelial cell morphogenesis and angiogenesis. Am J Pathol. 2000; 156: 899-909.

Ozeki Y, Matsui T, Yamamoto Y, Funahashi M, Hamako J, Titani, K. Tissue fibronectin is an endogenous ligand for galectin-1. Glycobiology 1995; 5:255-61.

Pacis R A, Pilat M J, Pienta K J, Wojno K, Raz A, Hogan V, Cooper C R. Decreased galectin-3 expression in prostate cancer. Prostate. 2000, 44:118-23.

Park J W, Voss P G, Grabski S, Wang J L, Patterson R J. Association of galectin-1 and galectin-3 with Gemin4 in complexes containing the SMN protein. Nucleic Acids Res. 2001; 29:3595-602.

Paz A, Haklai R, Elad-Sfadia G. Ballan E, Kloog Y. Galectin-1 binds oncogenic H-Ras to mediate Ras membrane anchorage and cell transformation. Oncogene. 2001; 20:7486-93.

Perillo N L, Marcus M E, Baum L G. Galectins: versatile modulators of cell adhesion, cell proliferation, and cell death. J Mol Med. 1998; 76:402-12.

Perillo N L, Pace K E, Seilhamer J J, Baum, L G. Apoptosis of T cells mediated by galectin-1. Nature 1995; 378:736-9.

Puche A C, Poirier F, Hair M, Barlett P F, Key B. Role of galectin-1 in the developing mouse olfactory system. Dev Biol. 1996; 179:274-87.

Rabinovich G A, Rubinstein N, Toscano M A. Role of galectins in inflammatory and immunomodulatory processes. Biochim Biophys Acta 2002; 1572:274-84.

Rabinovich G A, Toscano M A, Ilarregui J M, Rubinstein N. Shedding light on the immunomodulatory properties of galectins: novel regulators of innate and adaptive immune responses. Glycoconj J. 2004; 19:565-73.

Rosenberg I, Cherayil B J, Isselbacher K J, Pillai S. Mac-2-binding glycoproteins. Putative ligands for a cytosolic beta-galactoside lectin. J Biol Chem. 1991; 266:18731-6.

Rubinstein N, Alvarez M, Zwirner N W, Toscano M A, Ilarregui J M, Bravo A, Mordoh J, Fainboim L, Podhajcer O L, Rabinovich G A. Targeted inhibition of galectin-1 gene expression in tumor cells results in heightened T cell-mediated rejection; A potential mechanism of tumor-immune privilege. Cancer Cell. 2004; 5:241-51.

Salvatore P, Benvenuto G, Caporaso M, Bruni C B, Chiariotti L. High resolution methylation analysis of the galectin-1 gene promoter region in expressing and nonexpressing tissues. FEBS Lett. 1998; 421:152-8.

Schwarz F P, Ahmed H, Bianchet M A, Amzel L M, Vasta G R. Thermodynamics of bovine spleen galectin-1 binding to disaccharides: correlation with structure and its effect on oligomerization at the denaturation temperature. Biochemistry. 1998; 37:5867-77.

Singal R, van Wert J, Bashambu M. Cytosine methylation represses glutathione S-transferase P1 (GSTP1) gene expression in human prostate cancer cells. Cancer Res. 2001; 61:4820-6.

Stewart D A, Cooper C R, Sikes R A. Changes in extracellular matrix (ECM) and ECM-associated proteins in the metastatic progression of prostate cancer. Reprod Biol Endocrinol. 2004; 2:2-14.

Su Z Z, Lin J, Shen R, Fisher P E, Goldstein N I, Fisher P B. Surface-epitope masking and expression cloning identifies the human prostate carcinoma tumor antigen gene PCTA-1 a member of the galectin gene family. Proc Natl Acad Sci USA. 1996; 93:7252-7.

Symons A, Cooper D N, Barclay A N. Characterization of the interaction between galectin-1 and lymphocyte glycoproteins CD45 and Thy-1. Glycobiology. 2000; 10:559-63.

Thompson I M, Pauler D K, Goodman P J, Tangen C M, Lucia M S, Parnes H L, Minasian L M, Ford L G, Lippman S M, Crawford E D, Crowley J J, Coltman C A Jr. Prevalence of prostate cancer among men with a prostate-specific antigen level=4.0 ng per milliliter. New Eng J Med. 2004; 350: 2239-46.

Van den Brule F, Califice S, Castronovo V. Expression of galectins in cancer: a critical review. Glycoconj J. 2004; 19: 537-42.

van den Brule F A, Waltregny D, Castronovo V. Increased expression of galectin-1 in carcinoma-associated stroma predicts poor outcome in prostate carcinoma patients. J Pathol. 2001; 193:80-7.

Vasta G R, Ahmed H, Amzel L M, Bianchet M A. Amphibian galectins: molecular structure, properties and evolution Trends Glycosci Glycotechnol. 1997; 9:131-44.

Vasta G R, Quesenberry M, Ahmed H, O'Leary N. C-type Lectins and Galectins Mediate Innate and Adaptive Immune Functions: Their Roles in the Complement Activation Pathway. Develop Comp Immunol. 1999; 23:401-20.

Vasta G R., Ahmed H, Du S-J, Henrikson, D. Galectins in teleost fish: Zebrafish (*Danio rerio*) as a model species to address their biological roles in development and innate immunity. Glycoconjugate J, 2004a; 21:503-21.

Vasta G R, Ahmed H, Odom E W. Structural and Functional Diversity of Lectin Repertoires in Invertebrates, Protochordates, and Ectothermic Vertebrates. Current Opinion Struct Biol. 2004b; 14:617-30.

Warfield P R, Makker P N, Raz A, Ochieng J. Adhesion of human breast carcinoma to extracellular matrix proteins is modulated by galectin-3. Invasion Metastasis. 1997; 17(2): 101-12.

Warnecke P M, Bestor T H. Cytosine methylation and human cancer. Curr Opin Oncol. 2000; 12:68-73.

Yang R-Y, Hsu D K, Liu F-T. Expression of galectin-3 modulates T cell growth and apoptosis. Proc Natl Acad Sci USA. 1996; 93:6737-42.

Yang R Y, Hsu D K, Yu L, Ni J, Liu F T. Cell cycle regulation by galectin-12, a new member of the galectin superfamily. J Biol Chem. 2001; 276:20252-60.

Yu F, Finley R L Jr, Raz A, Kim H R. Galectin-3 translocates to the perinuclear membranes and inhibits cytochrome c release from the mitochondria. A role for synexin in galectin-3 translocation. J Biol Chem. 2002; 277:15819-27.

Zhou Q, Cummings R D. L-14 lectin recognition of laminin and its promotion of in vitro cell adhesion. Arch Biochem Biophys. 1993; 300:6-17.

Zick Y, Eisenstein M, Goren R A, Hadari Y R, Levy Y, Ronen D. Role of galectin-8 as a modulator of cell adhesion and cell growth. Glycoconj J. 2004; 19:517-26.

TABLE 1

Summary of current status and expected results of galectin expression and their promoter methylation in BPH, PIN, and various stages of PC

| | gal3 | | gal8g | |
|---|---|---|---|---|
| | mRNA/ protein | Promoter methylation | mRNA/ protein | Promoter methylation |
| BPH | = | = | = | = |
| PIN | NP | NP | NP | NP |
| Stage I | NP | NP | > | < |
| Stage II | << | >> | >> | << |
| Stage III | < | > | > | < |
| Metastatic | > | < | NP | NP |

=, almost equal to normal prostate tissue; >, greater than normal; <, less than normal; NP, not predictable

---

What is claimed is:

1. A method for determining prostate cancer in a subject, the method comprising:
    obtaining a biological sample from the subject;
    determining promoter methylation level in said biological sample of Gal3 and Gal8g; and
    comparing promoter methylation levels relative to levels found in normal prostate tissue,
    wherein a decrease in the level of Gal8g promoter methylation and an increase in the level of Gal3 promoter methylation is an indication of prostate cancer in the subject and wherein the biological sample is selected from prostate tissue, urine and serum.

2. A method for determining Stage II prostate cancer in a subject, the method comprising:
    obtaining a biological sample from the subject;
    determining promoter methylation level in said biological sample of Gal3; and
    comparing promoter methylation level of Gal3 in said biological sample relative to a promoter methylation level of Gal3 in a normal biological sample of a same type,
    wherein the level of Gal3 in the sample is heightened Gal3 promoter methylation relative to the Gal3 promoter methylation level in the normal biological sample of a same type, and where the heightened Gal 3 promoter methylation is indicative of Stage II prostate cancer and wherein the biological sample is selected from prostate tissue, urine and serum.

3. A method for determining Stage II prostate cancer in a subject, the method comprising:
    obtaining a biological sample from the subject;
    determining promoter methylation level in said biological sample by PCR; and
    comparing promoter methylation level of Gal3 in said biological sample relative to a promoter methylation level of Gal3 in a normal biological sample of a same type,
    wherein the level of Gal3 in the sample is heightened Gal3 promoter methylation relative to the Gal3 promoter methylation level in the normal biological sample of a same type, and where the heightened Gal 3 promoter methylation is indicative of Stage II prostate cancer and wherein the biological sample is selected from prostate tissue, urine and serum.

4. The method of claim 2, wherein the biological sample is prostate tissue.

5. The method of claim 2, wherein the biological sample is urine.

6. The method of claim 2, wherein the biological sample is serum.

7. The method of claim 2, further comprising comparing the promoter methylation level of Gal3 in said biological sample relative to a promoter methylation level of Gal3 in a Stage III prostate cancer sample of a same type, wherein the Gal3 promoter methylation level in the sample is heightened relative to the Gal3 promoter methylation level in the Stage III prostate cancer sample and wherein the Gal3 promoter methylation level in the Stage III prostate cancer sample is heightened Gal3 promoter methylation relative to the Gal3 promoter methylation level in the normal biological sample.

8. The method of claim 3, further comprising comparing the promoter methylation level of Gal3 in said biological sample relative to a promoter methylation level of Gal3 in a Stage III prostate cancer sample of a same type, wherein the Gal3 promoter methylation level in the sample is heightened relative to the Gal3 promoter methylation level in the Stage III prostate cancer sample and wherein the Gal3 promoter methylation level in the Stage III prostate cancer sample is heightened Gal3 promoter methylation relative to the Gal3 promoter methylation level in the normal biological sample.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial
<220> FEATURE:
<223> OTHER INFORMATION: primer

<400> SEQUENCE: 1
taaggtggaa gtggtaaggg g                                              21

<210> SEQ ID NO 2
<211> LENGTH: 21
<212> TYPE: DNA
<213> ORGANISM: Unknown
<220> FEATURE:
<223> OTHER INFORMATION: source for SEQ ID NO: 1 primer
```

-continued

```
<400> SEQUENCE: 2
caaggtggaa gtggcaaggg g                                              21

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
ccccacacaa ctcaccactc                                                20

<210> SEQ ID NO 4
<211> LENGTH: 20
<212> TYPE: DNA
<213> ORGANISM: Unknown
<220> FEATURE:
<223> OTHER INFORMATION: source for SEQ ID NO: 3 primer

<400> SEQUENCE: 4
ccccgcgcag ctcaccgctc                                                20
```